(12) United States Patent
Xie et al.

(10) Patent No.: US 11,672,582 B2
(45) Date of Patent: *Jun. 13, 2023

(54) SURGICAL WIRE DRIVER CAPABLE OF AUTOMATICALLY ADJUSTING FOR THE DIAMETER OF THE WIRE OR PIN BEING DRIVEN

(71) Applicant: Stryker Corporation, Kalamazoo, MI (US)

(72) Inventors: Mark M. Xie, Kalamazoo, MI (US); Robert W. Childers, Trinity, FL (US)

(73) Assignee: Stryker Corporation, Kalamazoo, MI (US)

( * ) Notice: Subject to any disclaimer, the term of this patent is extended or adjusted under 35 U.S.C. 154(b) by 299 days.

This patent is subject to a terminal disclaimer.

(21) Appl. No.: 17/171,353

(22) Filed: Feb. 9, 2021

(65) Prior Publication Data

US 2021/0220035 A1 Jul. 22, 2021

Related U.S. Application Data

(60) Division of application No. 15/595,112, filed on May 15, 2017, now Pat. No. 10,925,657, which is a
(Continued)

(51) Int. Cl.
*A61B 17/88* (2006.01)
*A61B 17/16* (2006.01)
(Continued)

(52) U.S. Cl.
CPC ...... *A61B 17/8897* (2013.01); *A61B 17/1697* (2013.01); *A61B 34/71* (2016.02);
(Continued)

(58) Field of Classification Search
CPC ............ A61B 17/1697; A61B 17/8897; A61B 2017/00318; A61B 2017/00477; A61B 34/71
See application file for complete search history.

(56) References Cited

U.S. PATENT DOCUMENTS

| 3,698,058 | A | | 10/1972 | Reimer et al. |
| 4,157,714 | A | * | 6/1979 | Foltz ................. A61B 17/1628 606/300 |

(Continued)

FOREIGN PATENT DOCUMENTS

EP 2777552 A1 9/2014

OTHER PUBLICATIONS

EPO "International Search Report and Written Opinion for PCT App. No. PCT/US2015/061350", dated May 31, 2016.

*Primary Examiner* — Samuel S Hanna
(74) *Attorney, Agent, or Firm* — Howard & Howard Attorneys PLLC

(57) ABSTRACT

A wire driver for driving a wire or pin into living tissue includes a rotating drive shaft, a collet, and a wedge. The collet is held fast to the drive shaft and has a plurality of feet radially moveable relative for grasping the wire or pin. Each foot has an outwardly located curved ankle surface with a concave or convex profile. The wedge is disposed over the collet and is at least partly inside the bore of the drive shaft. The wedge rotates with the drive shaft and has a tapered inner surface in selective engagement with the curved ankle surfaces. The wedge is moveable longitudinally relative to the collet feet to bear against the feet and cause the feet to grasp the wire or pin. The wedge has a release position in which the wedge is spaced from the collet feet, releasing the wire or pin.

13 Claims, 32 Drawing Sheets

Related U.S. Application Data continuation of application No. PCT/US2015/061350, filed on Nov. 18, 2015.

(60) Provisional application No. 62/081,700, filed on Nov. 19, 2014.

(51) Int. Cl.
*A61B 34/00* (2016.01)
*A61B 17/00* (2006.01)

(52) U.S. Cl.
CPC .............. *A61B 2017/00318* (2013.01); *A61B 2017/00477* (2013.01)

(56) References Cited

U.S. PATENT DOCUMENTS

| | | |
|---|---|---|
| 5,743,310 A | 4/1998 | Moran |
| 5,827,263 A | 10/1998 | Furnish et al. |
| 5,902,306 A | 5/1999 | Norman |
| 6,591,719 B1 | 7/2003 | Poole et al. |
| 6,673,078 B1 | 1/2004 | Muncie |
| 6,776,072 B2 | 8/2004 | Poole et al. |
| 7,638,958 B2 | 12/2009 | Philipp et al. |
| 9,687,257 B2 | 6/2017 | Straslicka et al. |
| 10,925,657 B2 | 2/2021 | Xie et al. |
| 2009/0287225 A1 | 11/2009 | Olsen et al. |
| 2011/0270323 A1 | 11/2011 | Olsen et al. |
| 2012/0004665 A1 | 1/2012 | Defossez et al. |
| 2014/0276890 A1 | 9/2014 | Khosla et al. |
| 2015/0182230 A1 | 7/2015 | Belagali et al. |

\* cited by examiner

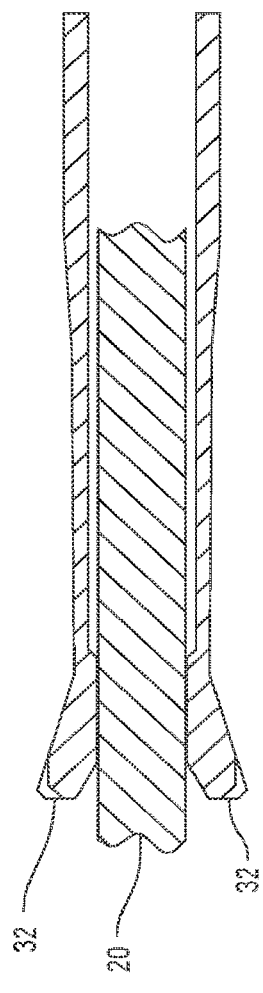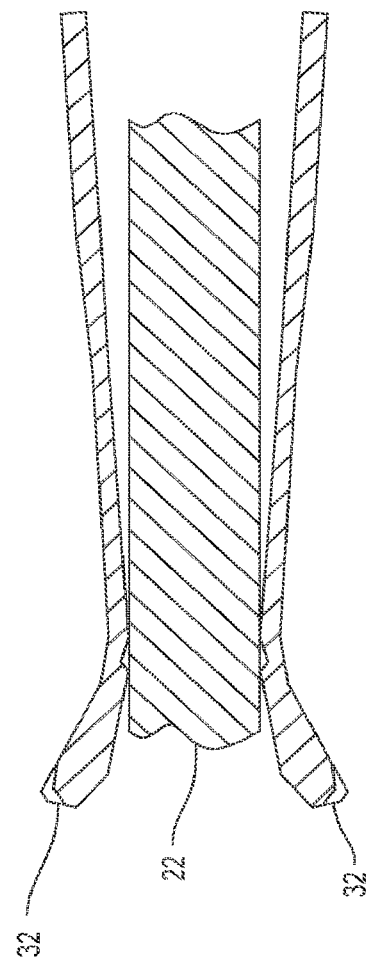

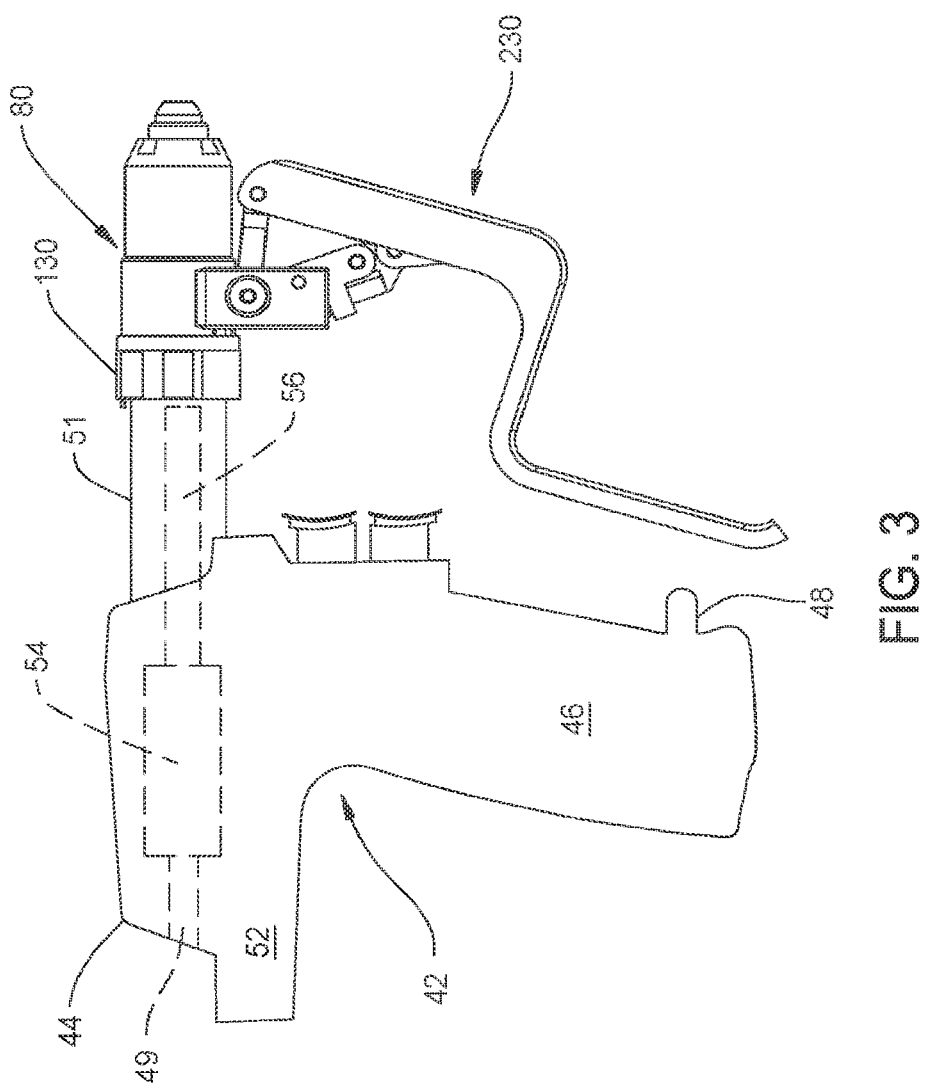

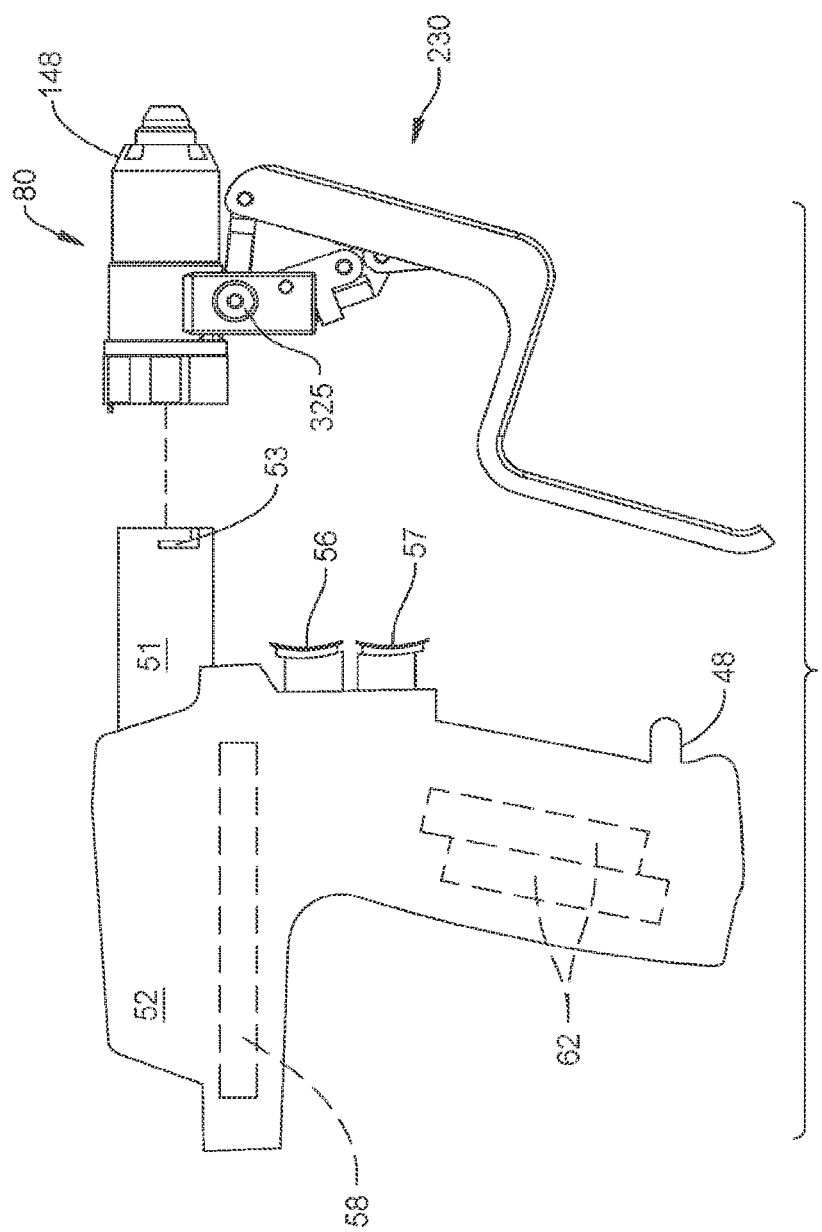

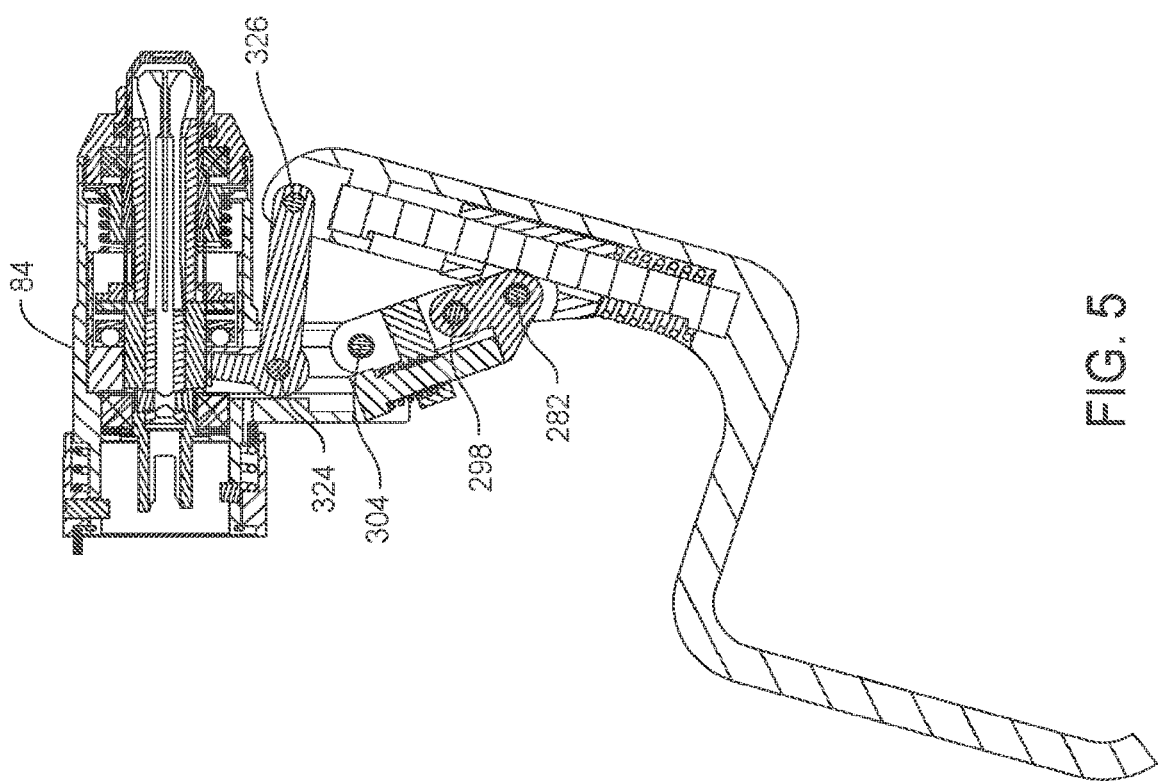

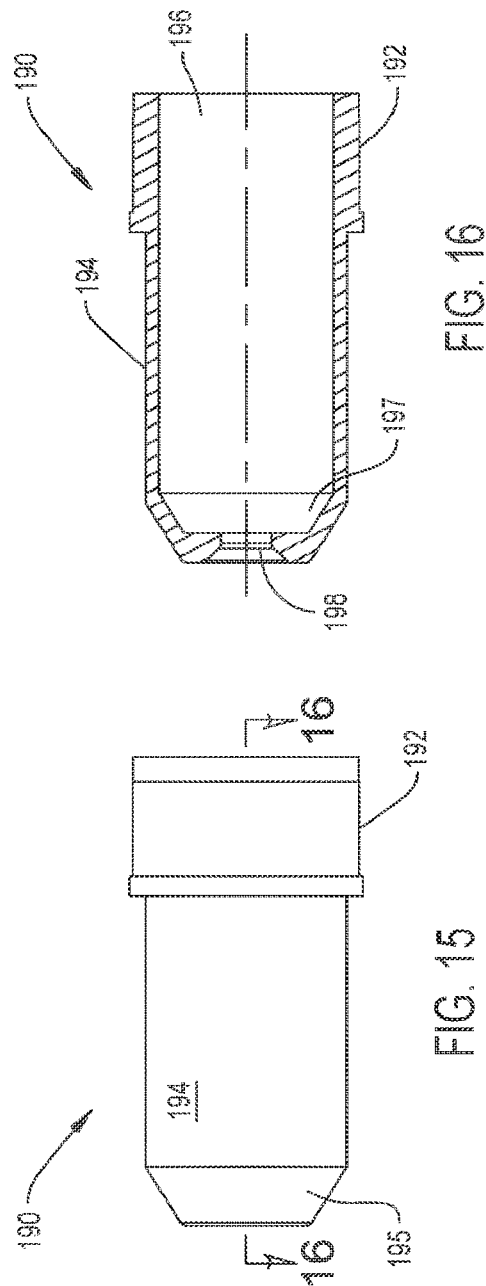

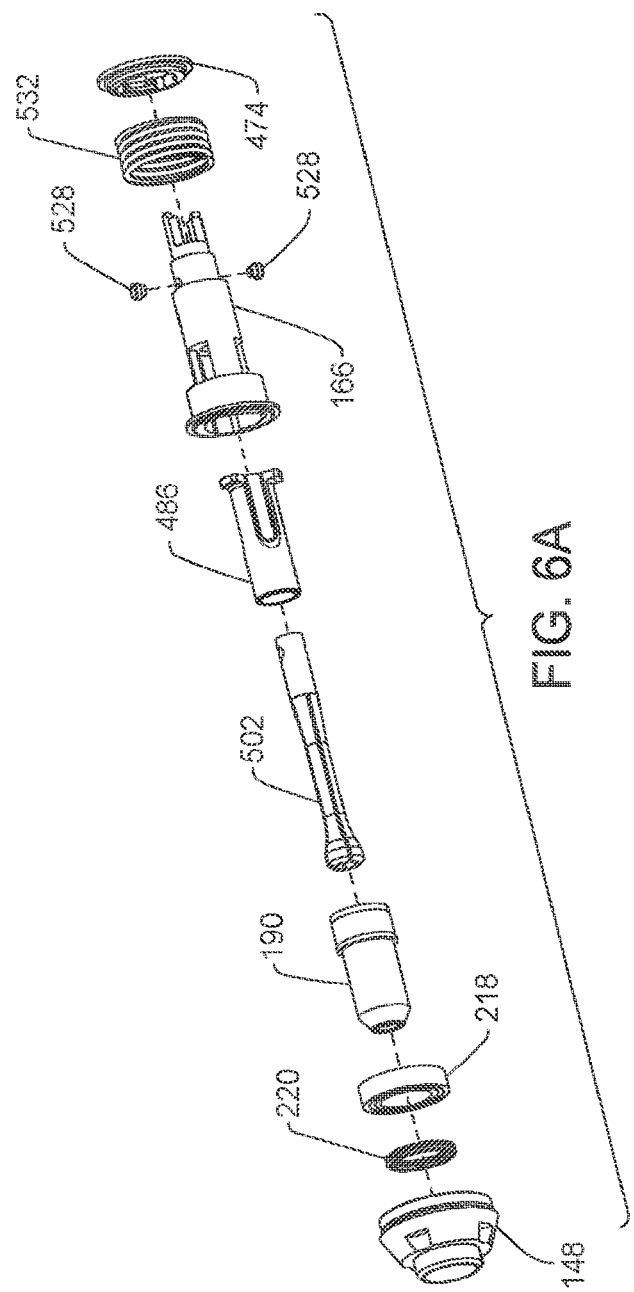

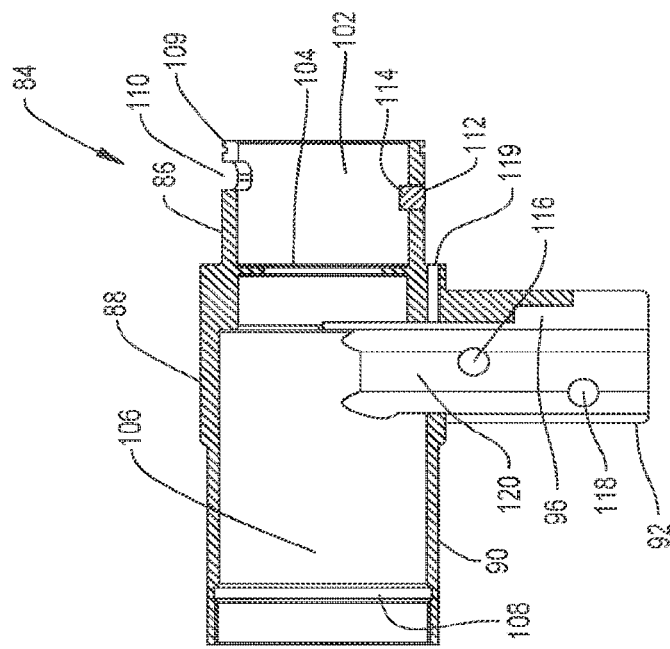
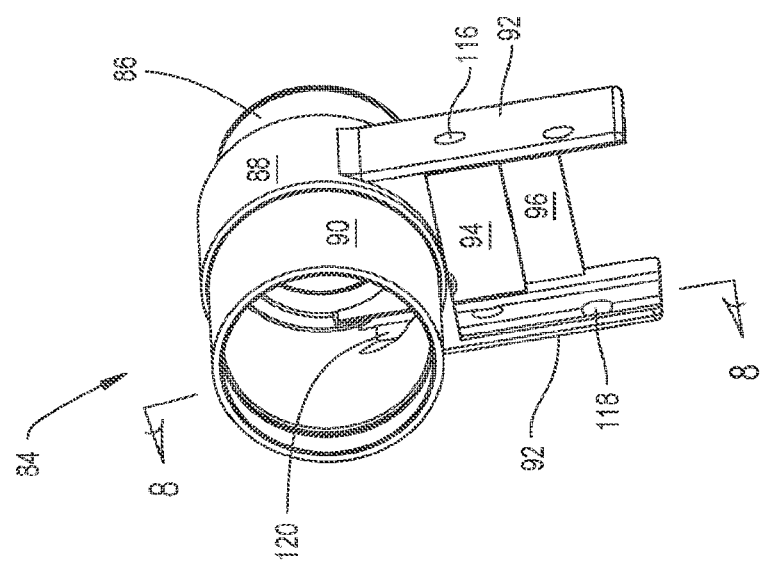

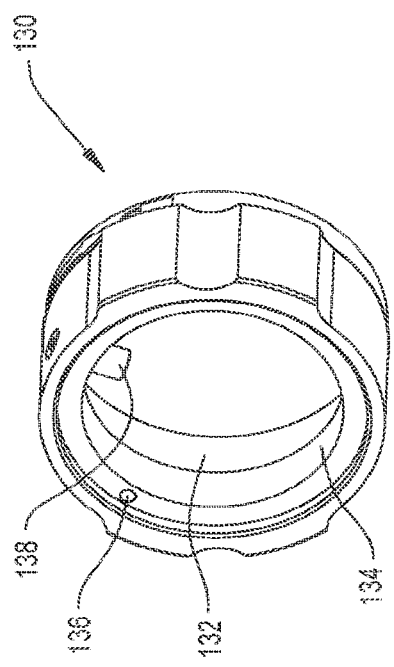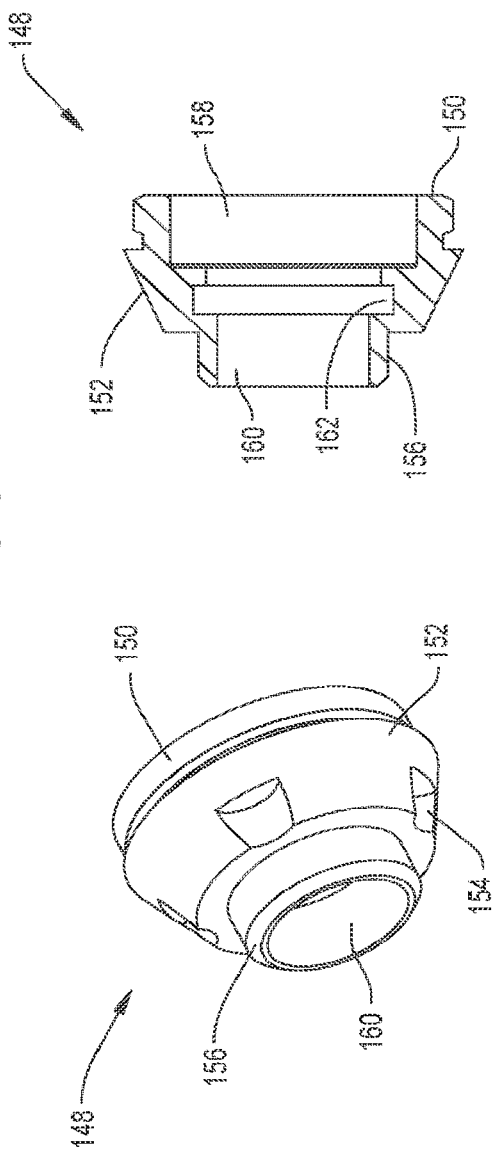

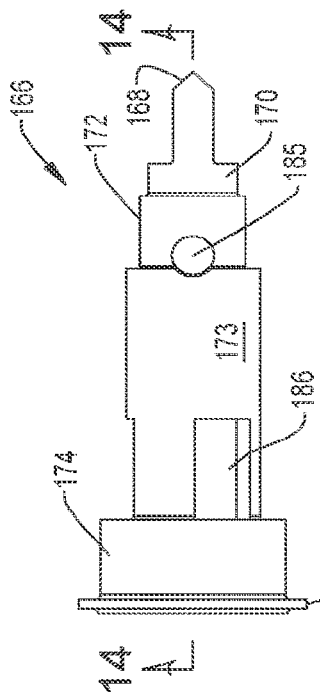
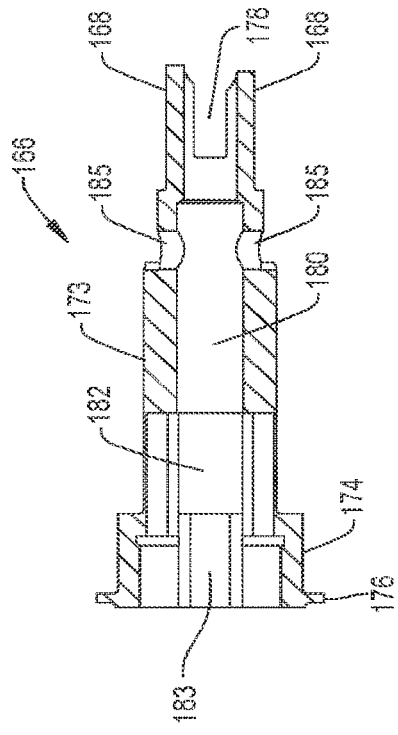
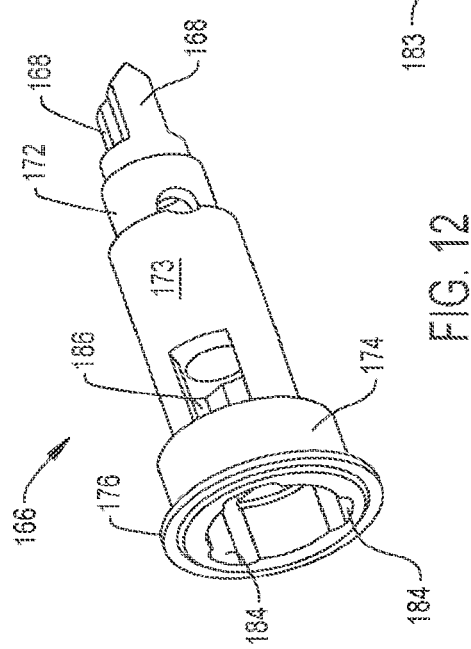

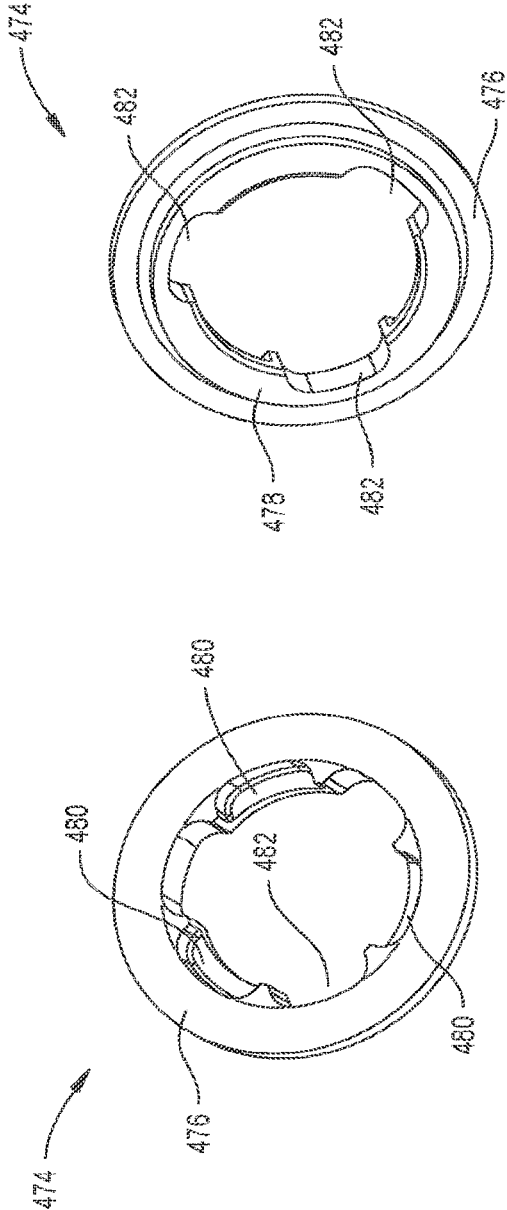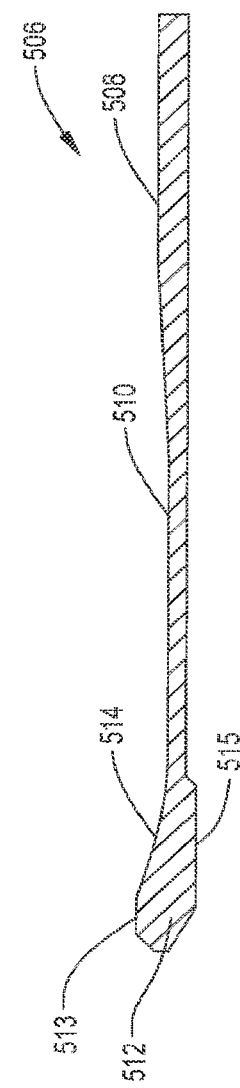

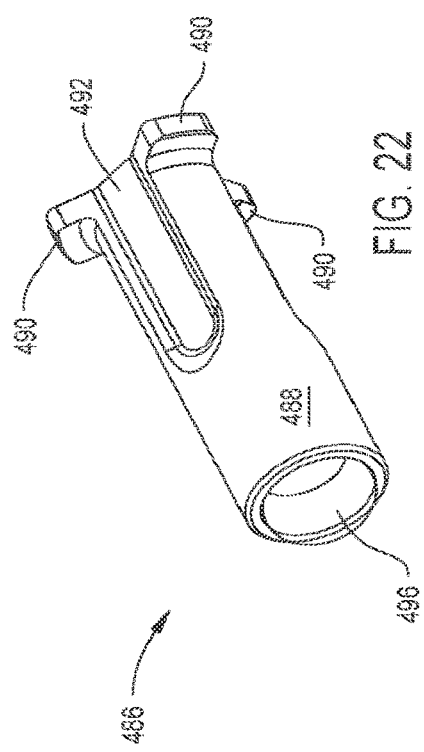
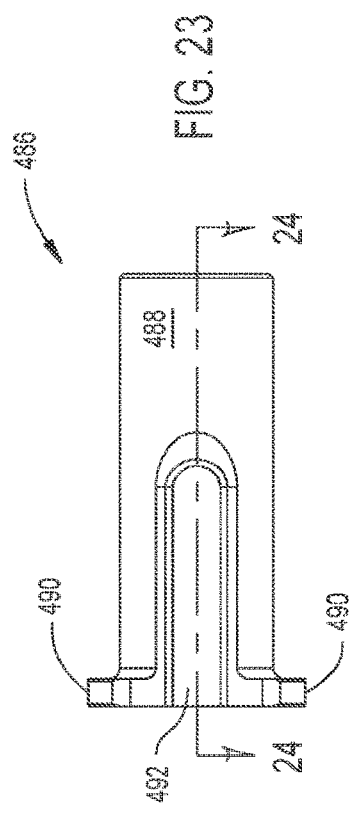
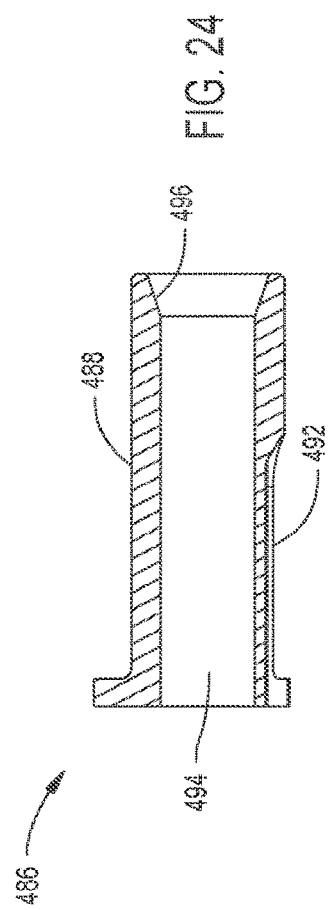

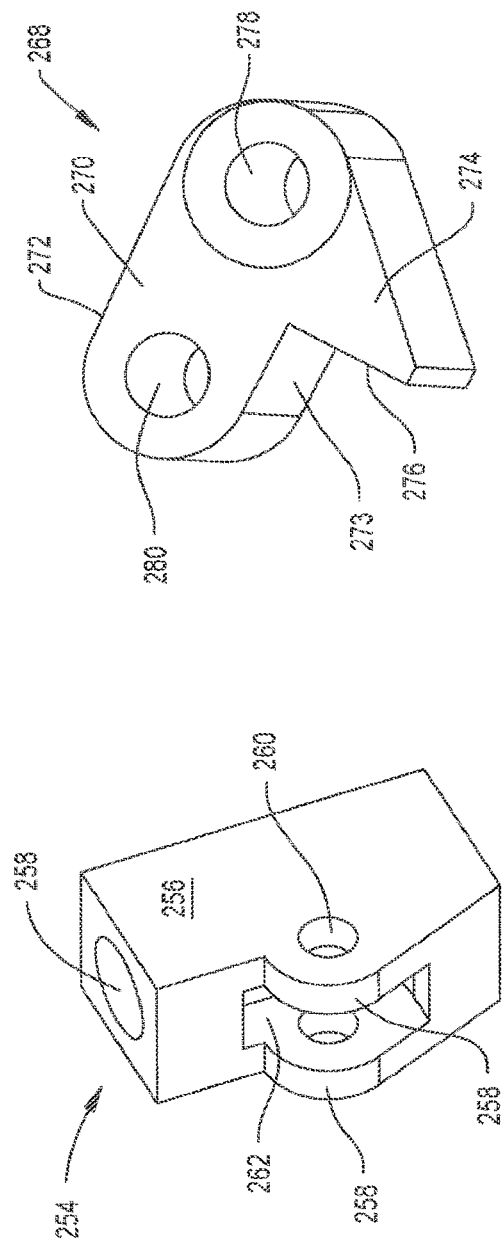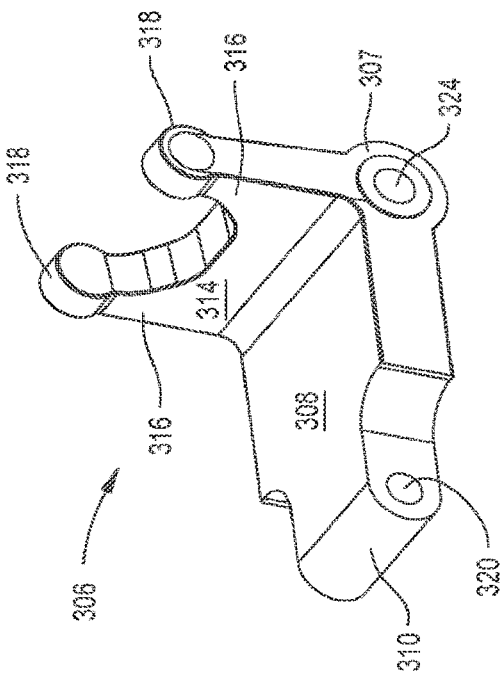

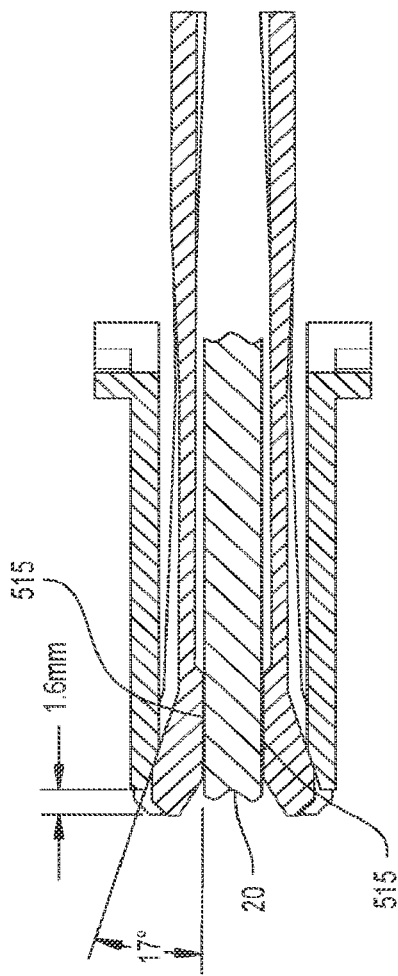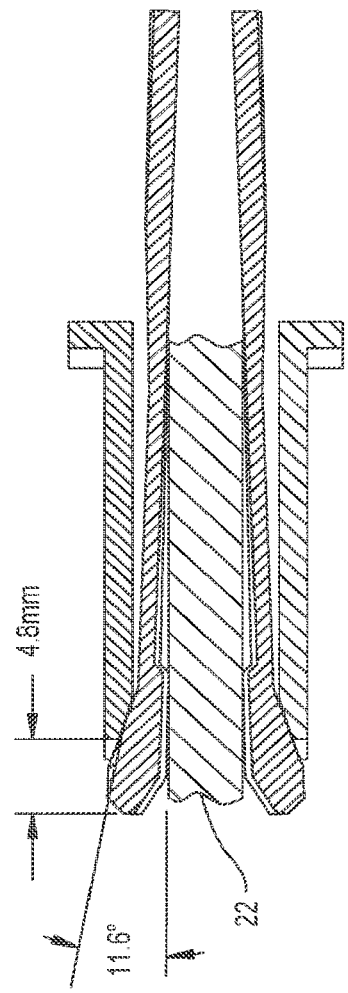

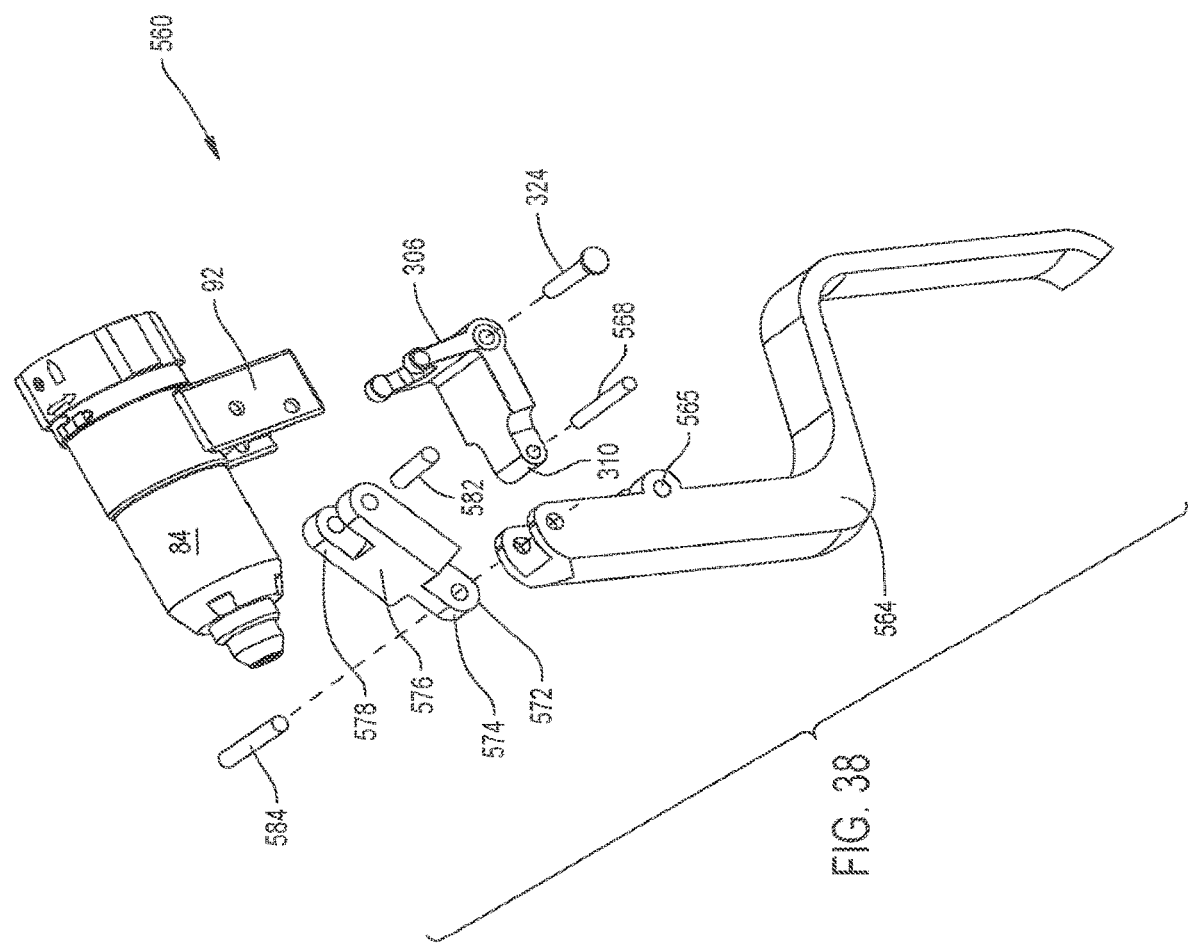

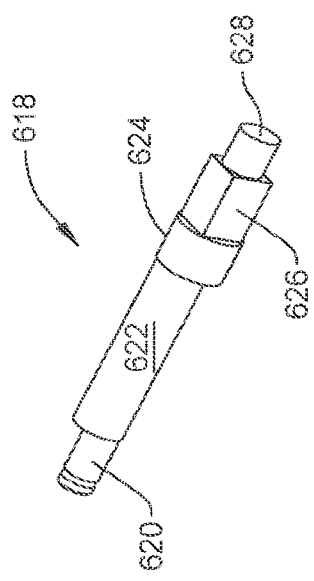
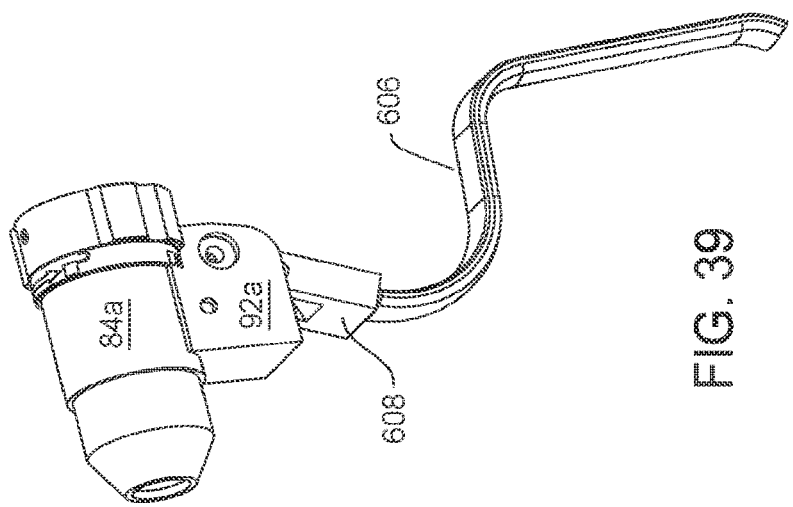
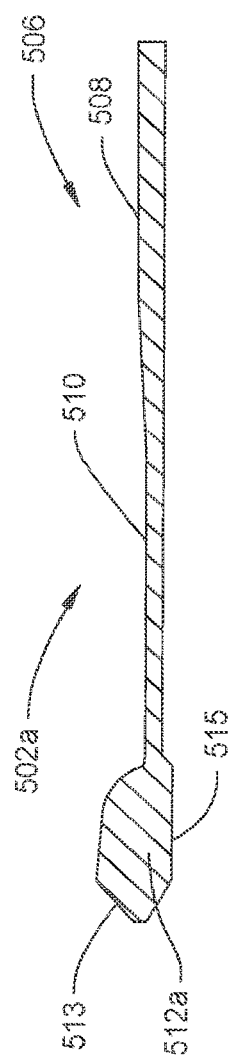

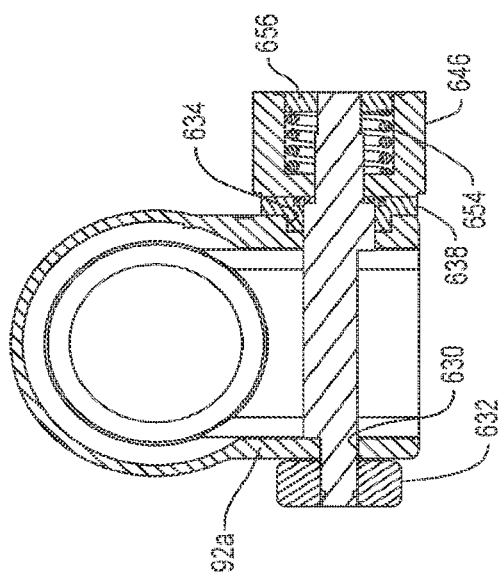
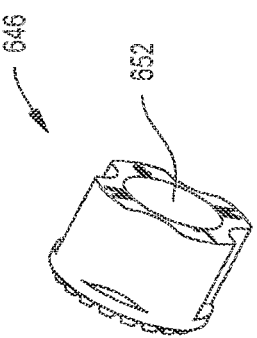
FIG. 42
FIG. 47
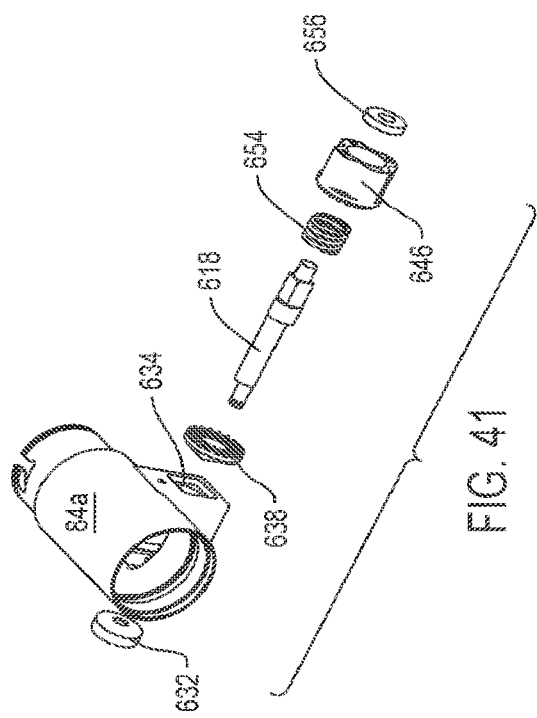
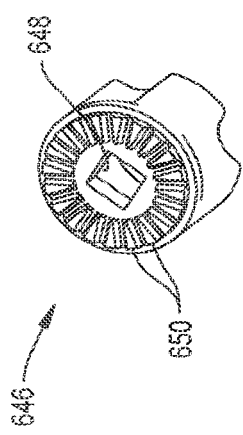
FIG. 41
FIG. 46

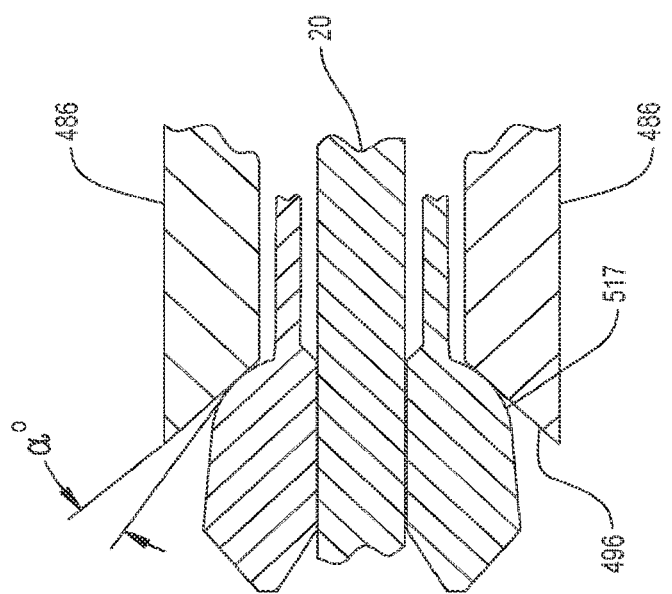

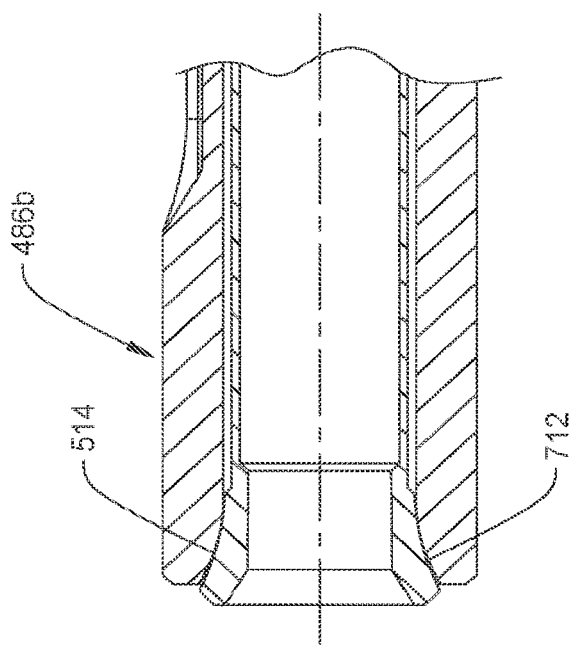

SURGICAL WIRE DRIVER CAPABLE OF AUTOMATICALLY ADJUSTING FOR THE DIAMETER OF THE WIRE OR PIN BEING DRIVEN

CROSS REFERENCE TO RELATED APPLICATIONS

This application claims priority to and the benefit of U.S. patent application Ser. No. 15/595,112, filed on May 15, 2017 which claims priority to and the benefit of International Patent Application No. PCT/US2015/061350, filed Nov. 18, 2015, which claims priority to and the benefit of U.S. Provisional Patent Application No. 62/081,700, filed on Nov. 19, 2014, each of which is hereby incorporated herein by reference in its entirety.

FIELD OF THE INVENTION

This invention relates generally to a wire driver used to drive a wire or a pin into a patient. The driver of this invention is able to drive the wire or pin into the patient with minimal, if any, adjustment due to the diameter of the wire or pin.

BACKGROUND OF THE INVENTION

A wire driver is a type of motorized surgical tool. Generally, a motorized surgical tool includes a handpiece in which a motor is housed. A wire driver includes a grasping mechanism that holds either a wire or a pin so that the wire or pin rotates upon actuation of the motor. The wire or pin is rotated so the wire or pin can be driven into tissue, typically bone. It is desirable so drive a wire or a pin into a bone to stabilize a fracture or a break in the bone. Both wires and pins are driven into a patient for this purpose. Alternatively, it may desirable to insert a pin into a patient to secure some sort of other implant, such as plate, to the bone.

A wire or a pin is an implant that is relatively small in cross sectional size. Many pins have a cross sectional diameter of 3.0 mm or less. A wire can have a diameter of 1.5 mm or less. Owing to the relatively small cross-sectional size of the wire or pin, there is a limit to the axial load to which the implant can be exposed before the implant will buckle or bend. It is thus a common practice to, when driving a wire or pin into bone, space the tip of the instrument used to perform this function a distance of 5 to 20 mm or less from the surface of the bone. This limits the axial load to which the wire or pin is exposed and the likelihood that the wire or pin will buckle.

The wire driver has features specifically designed to facilitate this type of insertion. Collectively, the grasping mechanism and motor form a cannula, a bore, in which the portion of the wire or pin not yet driven into the bone is housed. When it is time to drive a portion of the wire or pin into the patient, the grasping mechanism and motor are both actuated. This causes the wire or pin to rotate so the wire or pin can be driven into the patient. The exposed section of wire, the portion of the wire forward of the driver, is then driven into the patient. The grasping mechanism is then moved to the release state. The wire driver is then moved away from the patient to expose another section of the wire. Once an appropriate new length of the wire or pin is exposed, the grasping mechanism is reset to the grasping state. This newly exposed section of wire is then driven into the patient. The above steps are repeated until an appropriate length of the wire or pin is driven into the patient.

The grasping mechanism often consists of a set of collet feet that surround and normally lightly hold the wire or pin. This prevents the wire or pin from falling out of the wire driver. A wedge is disposed against the collet feet. The wedge drives the feet so the feet compress against the wire or pin more than when feet lightly hold the wire or pin. A lever, also part of the grasping mechanism, selectively moves the wedge into and out of engagement with the collet feet.

To manage costs, a hospital prefers to have a single tool able to drive into a patient both wires and pins. Traditionally, this tool is called a "wire driver" even though the tool is able to implant both wires and pins. This results in a design challenge because the diameter of these implants are, proportionally, very different. For example, a wire can have a diameter of 1.0 mm or less. A pin can have a diameter that of 3.0 mm or more.

A design challenge arises because the extent to which the wedge needs to be driven forward is inversely related to the diameter of the wire or pin being grasped. FIG. 2A illustrates the situation when a small diameter wire or pin 20 is disposed between the feet 32 of a collet. In FIGS. 1A-2B it is understood that plural collet feet 32 circumferentially surround and grasp the illustrated wires and pins 20 and 22. Since the wire or pin is of relatively small diameter, the wire or pin does appreciably flex the feet outwardly. This means the wedge 34 has to travel a relatively long distance before the wedge presses against the collet feet. In FIG. 2A this is shown by the indication that the when the distal end of the wedge 34 strikes the collet feet 32, the wedge is only 1.6 mm from the distal end of the collet feet.

FIG. 2B illustrates the situation in which a large diameter wire or pin 22 is disposed against the feet 22 of the collet. This larger diameter implant flexes the collet feet radially outwardly more than in comparison to the distance of flexure when small diameter pin is being grasped. Since the collet feet 32 are flexed outwardly further the wedge will strike the feet at a distance that is spaced further away from the distal end of the collet. In FIG. 2B this is shown by the indication that the when the wedge 34 strikes the collet feet 32 the wedge is 3.3 mm from the distal end of the collet feet.

This means that, when a lever is used to advance the wedge, the lever must be pivoted around a larger arc to grasp a small diameter wire than when the lever is pivoted to grasp a large diameter wire. The design challenge is present because this lever is typically located in front of the grip integral with the handpiece with which the wire drive is associated. The lever cannot be located so that the pivoting of the lever will be blocked by the abutment of the lever against the grip. To ensure that the lever has sufficient clearance to pivot when grasping a small diameter wire or pin one solution is to position the lever so it is spaced 4 cm or more from the handgrip. A problem arises because some surgeons, particularly surgeons with small hands, find it difficult to, with a single hand grip both the handgrip and the lever and pivot the lever.

This problem is exasperated when a wire or pin having a relatively large diameter is fitted to the same wire driver. As seen when comparing FIGS. 2A and 2B, this results in the wedge 34 having a static position that is proximally rearward of the position of the wedge when the small diameter wire or pin is fitted to the wire driver. By extension, this means that the lever used to advance the pin has a static position that is located further away from the handpiece grip. When the lever is so located relative to the grip, it can become even more difficult for the surgeon to grasp the lever in order to grasp the wire or pin in place so the wire or pin can be driven into bone.

One solution employed to overcome this problem is to mount the lever to the handpiece so the pivot axis can be shifted. More specifically, the pivot axis is shifted as function of the diameter of the wire or pin the wire driver is, for a given procedure, intended to drive. This makes it possible to provide a wire driver with a lever that, while not extending appreciably forward of the handgrip, is able to drive wires and pins over a wide range of diameters, less than 2.2 mm and greater than 3.0 mm.

A disadvantage of the above solution is that this requires the personnel in the operating room, prior to the use of the wire driver, set the lever to the appropriate position as a function of the diameter of the wire or pin. If the lever is not properly set at a minimum, it may be ergonomically difficult for the surgeon. In a more serious scenario, the wire driver may not be able to drive the wire or pin until the lever is properly set.

Still another disadvantage of current wire drives can be understood by reference to initial reference to FIGS. 1A and 1B. FIG. 1A illustrates the inside of the wire driver when a relatively small diameter wire or pin 20 is disposed in the collet. In FIG. 1A the wedge 34 is not shown. Owing to the relatively small diameter of this particular wire or pin 22, the wire or pin does not cause the collet feet to appreciably flex radially outwardly. Thus, as seen in FIG. 2A, when a wedge 34 is urged against the outer surface of the collet foot, the wedge is exposed to a surface that, relative to the longitudinal angle through the collet, is relatively shallow. In FIG. 2A this angle is shown as 17°. Owing to the wire or pin being relatively small in diameter and this angle being relatively small, when it is necessary to tightly grasp the wire or pin it is only necessary to apply a relatively low force.

FIG. 1B illustrates the situation when the wide diameter wire or pin 22 is seated in the same collet. Owing to the wide diameter of this wire or pin 22, the collet feet 32 are significantly flexed outwardly. In FIG. 1B, the angle of this flexure is exaggerated for purposes of illustration. This means that when the wedge is advanced against the collet feet 32 to compress the feet inward, the outer surfaces of the collet feet 22 are at an acute angle relative longitudinal axis of the collet feet that is relatively steep. As seen in FIG. 2B, this means that when the wedge 34 is pressed against the collet feet, the feet present a relative steep surface to the wedge. More specifically this surface is at a steeper angle to the wedge than when the collet is used to grasp a small diameter wire or pin. In FIG. 2B this angle is called out as 18°. In other words, the mechanical advantage of the wedge is reduced. The increased steepness of this angle means that, in comparison to when the wire driver is used to hold a small diameter wire or pin, the force needs to grip and driver the larger diameter wire or pin 22 is greater. Moreover, a larger diameter wire or pin is subjected to more resistance by bone when the wire or pin is driven into the bone. This means that, in comparison to a small diameter wire or pin, more force needs to be applied to the larger diameter wire or pin to ensure that the torque of the drive shaft is transferred to the wire or pin. Thus, in comparison to when a small diameter wire or pin is driven, the surgeon needs to manually apply an appreciably larger force to the larger diameter wire or pin to both grasp the implant and ensure that it will rotate when pressed against bone. If a surgeon needs to apply a significant amount of force to drive plural pins or wires into a patient, the need to perform this activity over an extended period of time can fatigue the surgeon.

SUMMARY OF THE INVENTION

This invention is related to a new and useful wire driver. The wire driver of this invention drives wires and pins into living tissue even though the wires and pins may have significantly different diameters. The wire driver of this invention drives wires and pins of different diameters into a tissue without first requiring that the driver be configured as a function of the diameter of the wire or pin being driven.

The wire driver of this invention includes a plural bar linkage that is manually actuated to actuate the driver grasping mechanism. At a minimum, the wire driver of this invention includes a two-bar linkage. In many preferred versions of the invention the wire driver of this invention includes a four-bar linkage.

One of the links of the wire driver of this invention is the lever. The lever is the link that is pivoted by the surgeon to place the grasping mechanism in the grasping state in which the wire or pin is connected to the motor to rotate upon actuation of the motor. A second link is the actuator link. The actuator link is connected at one end to the trigger. The opposed end of the actuator link is connected to the grasping mechanism. The displacement of the lever results in the actuator link urging the grasping assembly into grasping state.

In versions of the invention with three or more links one or more intermediate links connect the lever to a static point.

It is feature of some versions of this invention that the collet and/or wedge are designed so that, independent of the extent to which the collet feet are flexed, the angle at which the wedge meets the collet feet is minimized. In one version of the invention, this is accomplished by varying the angle of the outer surfaces of the collet feet so the acute angle relative to the longitudinal axis varies over the length of the feet. More particularly, the feet are shaped so this angle increases extending proximally to distally along the collet feet. In some versions of the invention, the angle varies by shaping the collet feet so they have ankle surfaces with a concave profile. In other versions of the invention the collet feet have ankle surfaces with a convex profile.

BRIEF DESCRIPTION OF THE DRAWINGS

The invention is pointed out with particularity in the claims. The above and further features and benefits of this invention are understood from the following Detailed Description and the accompanying drawings in which:

FIGS. 1A and 1B are cross sectional views depicting the extent the flexure of a foot collet varies of a function of the diameter of the wire or pin against which the foot is disposed.

FIG. 3 is side plane view of a handpiece with wire driver constructed in accordance with this invention;

FIG. 4 is an exploded view that depicts how the wire driver is removably attached to the handpiece;

FIG. 5 is a cross sectional view of the wire driver;

FIG. 6 is an assembly drawing depicted how FIGS. 6A and 6B form an exploded view of the wire driver of this invention;

FIGS. 6A and 6B are exploded views that, when assembled together, illustrate the wire driver of this invention;

FIG. 7 is a perspective view of the shell of the wire driver attachment;

FIG. 8 is a cross sectional view of the shell;

FIG. 9 is a perspective view of the lock collar;

FIG. 10 is a perspective view of the nose;

FIG. 11 is cross sectional view of the nose;

FIG. 12 is a perspective view of the wire driver drive shaft;

FIG. 13 is a side plan view of the drive shaft;

FIG. 14 is a cross sectional view of the drive shaft;

FIG. 15 is a plan side view of the nose;

FIG. 16 is a cross sectional view of the nose;

FIG. 20 is a perspective view of the proximally directed face of the spring retainer of the wire driver;

FIG. 21 is a perspective view of the distally directed face of the spring retainer;

FIG. 22 is a perspective view of the wedge of the wire driver;

FIG. 23 is a side plan view of the wedge;

FIG. 24 is a cross sectional view of the wedge taken along line 24-24 of FIG. 23;

FIG. 27A is a cross sectional view of the distal end of the collet the view being rotated 90° from the view of FIG. 27.

FIG. 30 is a perspective view of the slide;

FIG. 33 is a perspective view of the cam link; and

FIG. 34 is a perspective view of the actuator link;

FIGS. 35A and 35B are cross sectional view depicting the flexure of the collet feet of the collet of this invention and the extent to which the associated wedge moves over the feet to clamp, to grasp, the underlying wire or pin to the collet;

FIG. 38 is an exploded view of the wire driver of FIG. 37;

FIG. 39 is a perspective view of a second alternative wire driver of this invention;

FIG. 41 is an exploded view of the assembly holding the lever pivot pin of the wire driver of FIG. 39;

FIG. 42 is a cross sectional view of the assembly of FIG. 40;

FIG. 43 is a perspective view of the lever pivot pin;

FIGS. 46 and 47 are perspective views of different angles of the control knob of the assembly of FIG. 41;

FIG. 50 is a cross section view of an alternative collet that is part of this invention;

FIG. 51 is a cross sectional view of the collet of FIG. 50 grasping a small diameter wire or pin;

FIG. 54 is a cross sectional view of how the alternative wedge of FIG. 53B presses against the ankle surfaces of a collet;

DETAILED DESCRIPTION

I. First Embodiment

Figure 2A:
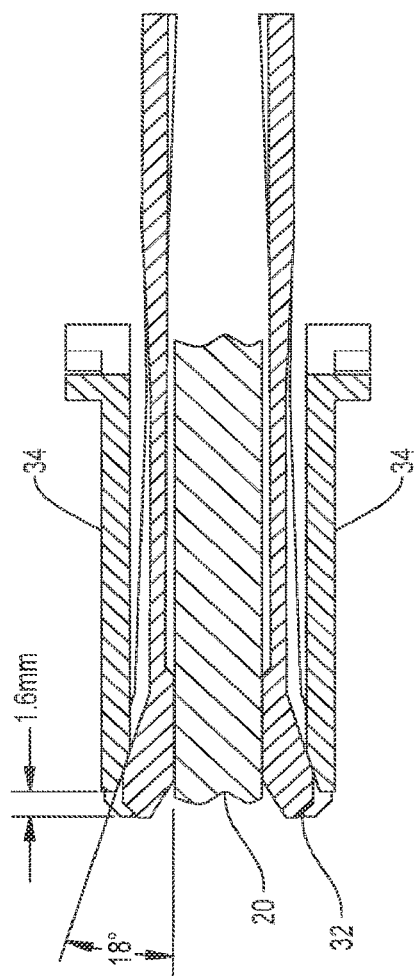
FIGS. 2A and 2B are cross sectional views depicting how, in the prior art, as result of the varying in the flexure of the collet foot as a function of wire or pin diameter, the position at which the wedge abuts the feet varies and the angle at which the wedge presses against the feet also varies.
Figure 2B:
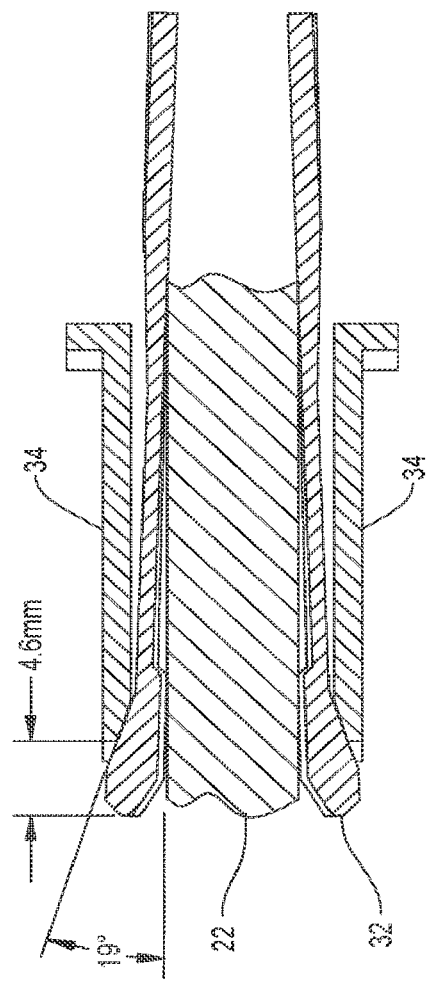

FIGS. 3 and 4 provide an overview of the wire driver of this invention. In the depicted version of the invention, the wire driver consists of a handpiece 42 to which a wire driver attachment 80 is removably attached. Handpiece 42 includes a housing or shell that forms the body 44 of the handpiece. The depicted handpiece 42 is pistol shaped. The body 44 includes a handgrip 46. A finger 48 extends distally forward from the distally directed surface of the handgrip 46. (Here "distal" is understood to mean away from the practitioner holding the handpiece, towards the site at which the wire or pin is to be driven into patient. "Proximal" is understood to mean towards the practitioner holding the handpiece, away from the site at which the wire or pin is to be fitted.) A barrel 52 is located above the handgrip 46. The barrel 52 extends both distally forward from and proximally away from the handgrip 46. A head 51 extends distally forward from the barrel. While not illustrated, the head 51 has an open distal end. Head 51 is further formed to have a generally L-shaped slot 53. The section of the slot 53 that is parallel with the longitudinal axis of the barrel 52 extends proximally from the distal end of the head 51. The arcuate section of slot 53 is spaced away from the distal end of the head 51.

Internal to the barrel is a motor 54, represented as phantom cylinder. Motor 54 supplies the power for driving the wire or pin. Motor 54 includes an output shaft 56, also seen as a phantom cylinder. Not illustrated and not part of the present invention is the gear assembly that reduces the speed/increases the torque of the output shaft relative to the rotor that is actually rotated by the motor stator. Output shaft 56 extends into the open end of head 51. The motor output shaft 56 is formed with a lumen or through bore that extends proximally to distal through the shaft (lumen not identified). Internal to the barrel 52 a tube 49, shown as phantom cylinder to the motor shaft. The lumen through the tube 49 opens into the lumen internal to the output shaft 56. Collectively, the lumen through the tube 49 and the lumen through the output shaft 56 serve as a conduit through which wire or a pin is fed from the proximal end of the handpiece into the wire driver attachment 80.

In the described version of the invention, motor 54 is an electric motor. Batteries 62, shown as dashed rectangles, are disposed in the handgrip 46. The batteries 62 provide the charge for energizing the motor. Triggers 55 and 57 extend distally forward from and is moveably mounted to the handgrip 46. Internal to the barrel 52 is a control module 58, represented by a rectangle. Control module 58 includes components able to: monitor whether or not one of the triggers 55 and 57 has been depressed; and, based on the depression of the triggers, apply a current to the motor 54 from the batteries 62 that results in the actuation of the motor desired by the surgeon. The specifics of the handpiece assembly are not part of the present invention. Examples of handpiece include the control modules are disclosed in the Applicant's U.S. Pat. No. 7,638,958 and its US Pat. Pub. No. 2015/0182230 A1/PCT Pub. No. WO 2013/177423, the contents of which are explicitly incorporated herein by reference.

Wire driver attachment 80 is removably fitted to handpiece head 51. To minimize verbiage, the wire driver attachment 80 will at times in this document be referred to as the wire driver 80. It will further be understood that a wire driver of this invention may also include a single piece handpiece that includes both wire driving assembly now described and the motor that actuates the wire driving assembly.

Wire driver 80 includes a housing 84 now described by reference to FIGS. 7 and 8. A cylindrically shaped foot 86 forms the proximal end of the housing 84. A trunk 90, integral with foot 86, extends forward from the foot. Trunk 90 is also cylindrical. The outer diameter of the trunk 90 is greater than the outer diameter of the foot 86. In the depicted version of the invention, the housing is further formed to have circularly shaped ring 88 that protrudes radially outwardly from the trunk 80 Ring 88 extends over the portion of the trunk 90 immediately distal to the foot 86.

Two parallel legs 92 extend downwardly from the opposed sides of housing trunk 90. More particularly, the legs 92 extend downwardly from the ring 88. Legs 92 are in planes parallel to the proximal-to-distal longitudinal axis of the wire driver 80. A panel 94 extends downwardly from the ring 88 and between legs 92. Panel 94 extends between legs 92 adjacent the proximal ends of the legs. The panel 94 does not extend the whole length of the legs. Instead, the panel 94 extends a distance that is approximately three-fourths the overall length of the legs 92. The panel 94 is formed so there is a step 96 in the distally directed face of the panel. The distally directed face of step 96 is recessed proximally relative to the rest of the panel 94.

Housing 84 is formed to have a bore 102 that extends from the proximal end of the housing towards feet 86. Bore 102 extends into a portion of the trunk 90 subtended by ring 88. The housing 84 is formed so that an annular rib 104 extends inwardly from the inner wall of the housing that defined bore 90 Forward of rib 104, bore 102 opens into a bore 106. Bore 106 has a diameter greater than that of bore 102. The inner wall of the housing that defines bore 106 is formed to define a groove 108 that extends circumferentially around and radially outwardly from bore 94. The housing is formed so that groove 108 is located a short distance proximal to the open distal end of bore 106. While not illustrated, the portion of the inner cylindrical wall of the housing trunk 90 forward of groove 108 is provided with threading.

Housing 84 is further formed to have a groove 109 that extends circumferentially around and radially inward of foot 86. Groove 109 is located immediately forward the proximal end of the foot 86, which is also the proximal end of the housing 84. Forward of groove 109, foot 86 is formed to have an arcuately shaped slot 110. Slot 110 extends into bore 102. The housing 110 is shaped so that slot 110 subtends an angle of approximately 23° around the outside of foot 86.

Forward of slot 110, the foot 86 is shaped to have through hole 112. A pin 114 is seated in hole 112. Pin 114 projects into bore 102.

Each leg 92 of the housing 84 is formed with two bores. A first bore, bore 116, is located proximal to where the leg 92 extends downwardly from the ring 88. Bores 116 are coaxial. A second bore, bore 118, is located distal to and below the bore 116. Bores 118 are coaxial. A closed end bore 119 is formed in housing ring 88. Bore 19 extends distally forward from the proximally directed surface of the ring 88. The housing 84 is formed so that bore 119 is located in the portion of the ring 88 located between legs 92. Wire driver housing 84 is further formed to have an opening 120 that extends through stave 88. Opening 120 extends between legs 92 through the bottom of the housing. Opening 120 provides access into housing bore 106.

Figure 6B:
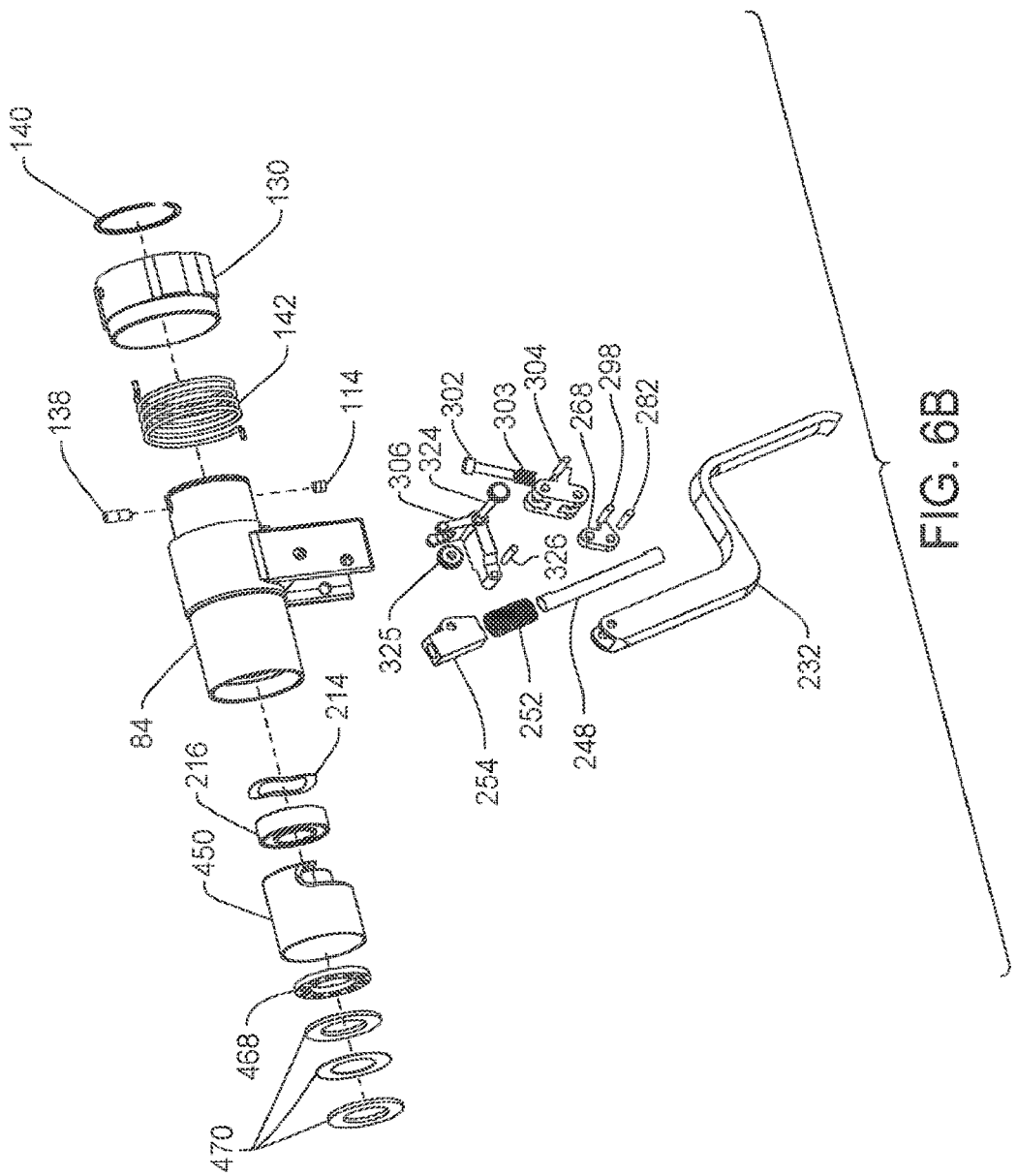

A lock collar 130, seen best in FIGS. 6B and 9, is rotatably fitted over the housing foot 86. Lock collar 130 is generally tubular in shape. Not identified is the knurling on the outer surface of the collar 130 that facilitates finger gripping and rotation of the collar. A bore 132 extends proximally to distally through the collar 130. The lock collar 130 is further formed to have rib 134 that extends inwardly from the inner surface of the collar that defines bore 132. The collar 130 is formed so that rib 134 extends radially inwardly from the bore-defining surface at a location spaced approximately 2 to 10 mm distally forward of the proximal end of the collar. The rib 134 subtends a length equal to approximately 20 to 30% of the overall length of the collar. Rib 134 has an inner diameter that is incrementally greater than that of the housing foot 86 to allow the collar to rotate, but not wobble, over the foot.

Rib 134 is formed to have a closed end bore 136. Bore 136 is centered on a longitudinal axis that is parallel to the proximal to distal longitudinal axis through the collar 130. A pin 138 is mounted to rib 134. Pin 138 is centered on a line that radiates from the longitudinal center axis of the collar 130. The pin 138 projects into bore 132. Not identified is the hole in the collar 130 in which the outer end of the pin 138 is seated. Pin 138 is dimensioned so that the portion of the pin disposed in the collar bore 132 can seat in slot 53 formed in the handpiece head 51

When the wire driver attachment 80 of this invention is assembled, the lock collar 130 is disposed over the housing foot 86. The collar 130 is positioned so that the collar rib 134 is located slightly forward of the groove 109 formed in the housing foot 86. Pin 138 is pressed into the collar 130 so the inner portion of the pin extends through housing slot 110 and into housing bore 102. A snap ring 140, identified in FIG. 6B, is fit in the housing groove 109. The outer perimeter of the snap ring 140 projects into collar bore 136. The outer diameter of the snap ring 140 is greater than the outer diameter of the lock collar rib 134. The abutment of the rib 134 against snap ring 140 limits the extent to which the lock collar 130 can be pulled proximally relative to the housing 84.

A helical torsion spring 142, seen best in FIG. 6B, is located between the housing foot 86 and the inner surface of the lock collar 130 that defines bore 132. Spring 142 is located forward of the collar rib 134. Legs, not identified, extend outwardly from the opposed ends of spring 142. The legs are located on parallel axes that are parallel to the proximal to distal longitudinal axis through the spring 142. When wire driver 80 is assembled, the distally directed spring leg is seated in housing bore 119. The opposed proximally directed leg is seated in lock collar bore 136. Upon assembly of attachment 80, the components are arranged so that the spring 142 is preloaded. Spring 142 places a torsional force on the lock collar 130 that urges the lock collar into rotation. The spring-induced rotation of the lock collar 130 is limited by the abutment of pin 138 against the section of the housing that defines one end of slot 110. Finger force is all that is required to rotate the lock collar in opposition to the force the spring imposes on the collar 130.

A cap 148, now described by reference to FIGS. 10 and 11, is secured over the open distal end of the housing trunk 90. Cap 148 is formed to have a ring-shaped base 150. The outer surface of the base 150 is provided with threading, not illustrated. When wire driver 80 is assembled, the threaded base 150 of cap 148 is screw secured to threading around the most distal end of housing bore 106. Distally forward of base 150, the cap 148 has a shoulder 152. Immediately adjacent the base 150 the shoulder 152 has a diameter greater than that of hosing bore 106. During the process of assembling the wire driver 80, the abutment of cap shoulder 152 disposed over the distal end of the cap shoulder 152 against the adjacent distally directed end of the housing trunk 90 limits the extent to which the cap 148 is screw secured to the housing 84. Extending distally forward from the proximal end of the shoulder 152, the outer diameter of the shoulder decreases. Four indentations 154, one identified, are formed in the shoulder 152. Indentations 154 are present to receive a tool used to screw secure and remove the cap 148 from the housing 84.

A head 156 extends forward from the cap shoulder 152. The cap 148 is formed so that the head 156 is ring like in shape. The outer diameter of the head 156 is less than the outer diameter of the immediately adjacent portion of the shoulder 152.

Two contiguous bores form an opening through cap 148. A first bore, bore 158, extends distally forward from the proximal end of the cap 148. Bore 158 extends through base 150 and a short distance into the shoulder 152. The second bore, bore 160, extends forward from the distal end of bore 158. Bore 160 has a diameter less than the diameter of bore 158. Bore 160 extends through the shoulder 152 and head 156 so as to form the distal end opening into the cap 148. Within shoulder 152 cap 148 is formed to have a groove 162. Groove 162 extends radially outwardly from the inner cylindrical wall of the cap that defines bore 160.

A drive shaft 166 is rotatably disposed in the wire driver housing 84. The drive shaft 166, as best seen in FIGS. 12 through 14, includes at the most proximal end two legs 168. Legs 168 are diametrically opposed to each other relative to the proximal to distal longitudinal axis through the drive shaft 166. The legs 168 are dimensioned to seat in complementary slots formed in the handpiece output shaft 56 (output shaft slots not illustrated). The engagement of the attachment drive shaft legs 168 with the handpiece output shaft 56 causes the drive shaft 166 to rotate in unison with the handpiece output shaft 56. The distal ends of legs 168 extend to a ring-shaped belt 170. Legs 168 and belt 170 have a common outer radius of curvature.

Forward of the belt 170, the drive shaft 166 is formed to have waist 172. The driver shaft 166 is formed so that waist 172 has an outer diameter greater than the outer diameter of the legs 168 and belt 170. The drive shaft 166 is formed to have a torso 173 that is located immediately forward of waist 172. The cylindrical torso 173 has an outer diameter greater than that of the waist 172. A cylindrical head 174 is located immediately forward of the torso 173. Head 174 is formed to have an outer diameter greater than that of the torso 173.

A lip 176 extends radially outwardly from and circumferentially around the outer cylindrical surface of the head 174. Drive shaft 166 is formed so that lip 176 is located approximately 1 to 5 mm rearward of the distal end of the head 174.

The drive shaft 166 is formed with a number of voids. At the proximal end of the shaft there is the void space 178 between legs 168 and within belt 170. The portion of void space 178 within the belt 170 is understood to be circular in cross section, in planes perpendicular to the longitudinal axis through the drive shaft 166. A bore 180 extends forward of void space 178. Bore 180 extends through the shaft waist 172 and partially through the shaft torso 173. Bore 180 has a diameter greater than the diameter of the adjacent void space 178. Bore 180 extends approximately halfway through the shaft torso 173. Bore 180 opens into a bore 182. Bore 182 has a diameter greater than that of bore 180. Bore 182 extends through the distal portion of torso 173 and the proximal portion of the shaft head 174.

A bore 183 extends forward bore 182. Bore 183 extends through the shaft head 174 so as to form the distal end opening into the drive shaft 166. Bore 183 is larger in diameter than bore 182. The drive shaft 166 is further formed so that there are three grooves 184 in the inner cylindrical wall of the shaft that defines bore 183 (two grooves 184 identified in FIG. 12). Grooves 184 are thus contiguous with and extend radially outwardly from bore 183.

The drive shaft 166 has two coaxially aligned through holes 185. Holes 185 are centered on an axis that is perpendicular to the longitudinal axis through the drive shaft 166. Holes 185 extend through the shaft waist 172 into bore 180. A small section of each hole 185 also intersects the portion of the torso 173 immediately adjacent the waist 172. The shaft torso 173 is formed with three equiangularly spaced apart slots 186. Slots 186 are formed in the section of the torso 173 that defines bore 182 (one slot 186 identified in each of FIGS. 12 and 13). Slots 186 extend to bore 182. Each slot 186 is in registration with a separate one of the grooves 184 formed in the shaft head 174.

A nose 190, seen best in FIGS. 15 and 16, is seated in and extends forward from the drive shaft head 174. The nose 190 is formed to have a tube-shaped base 192. Base 192 is dimensioned to be press fit in bore 183 internal to drive shaft head 174. Extending distally forward from the base 192, nose 190 has a tube-shaped stem 194. The drive shaft 166 and nose 190 are collectively configured so that when the two components are fit together, the nose base 192 extends a short distance forward of the drive shaft. Stem 194 has an outer diameter that is less than the diameter of cap bore 160. More specifically, cap 148 and nose 190 are collectively dimensioned so that the nose stem 194 can freely rotate in cap bore 160.

The nose 190 is further formed to have a tip 195 that extends distally forward from the stem 194. Immediately forward of the stem 194 the tip 195 has an outer diameter that, extending distally, decreases.

A bore 196 extends distally from the proximal end of nose base 192. Bore 196 extends through the base 192 and stem 194 of the nose 190. The bore 196 is of constant diameter. Bore 196 opens into a bore 197 disposed in the tip 195. Bore 197 tapers with the taper of tip 195. The tip 195 has a disk-shaped, distally directed face (not identified). This face is formed with an opening 198. Opening 198 opens into bore 197.

The drive shaft 166 and nose 190 are rotatably mounted to the housing 84*b* as a single unit. A bearing assembly 216, seen best in FIG. 6B, extends between the inner surface of the housing that defines bore 102 and the outer surface of the drive shaft waist 172. Within housing bore 102, the outer race of bearing assembly 216 is located forward of the distally directed face of rib 104. A wave washer 214, seen in FIG. 6B, is disposed between rib 106 and the outer race of bearing assembly 216. The wave washer 214 urges the bearing assembly 216 distally forward. A bearing assembly 218 extends between cap 148 and nose 190. The outer race of bearing assembly 218 is seated against the inner cylindrical wall of the nose that defines cap bore 158. The inner race of bearing assembly 218 seats against the portion of the nose stem 194 immediately forward of base 192. The inner race of bearing assembly 218 actually rests against the annular distally facing step of the nose 190 that defines the transition from the base 192 to the stem 194.

The components forming the wire driver 80 are dimensioned so that when the wire driver is assembled, the nose stem extends through and forward from cap bore 160. A seal 220, seen best in FIG. 6A, is disposed in cap groove 162. Seal 220 abuts the nose stem 194 to provide a barrier across the gap between cap 148 and the nose 190.

Figure 18:
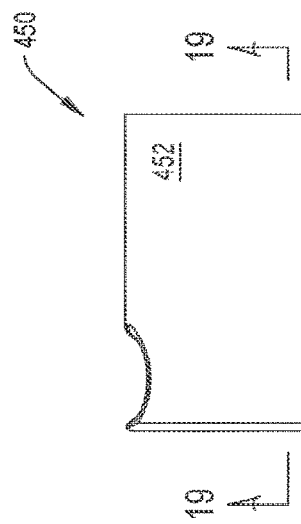
FIG. 18 is a top plan view of the thrust actuator.
Figure 19:
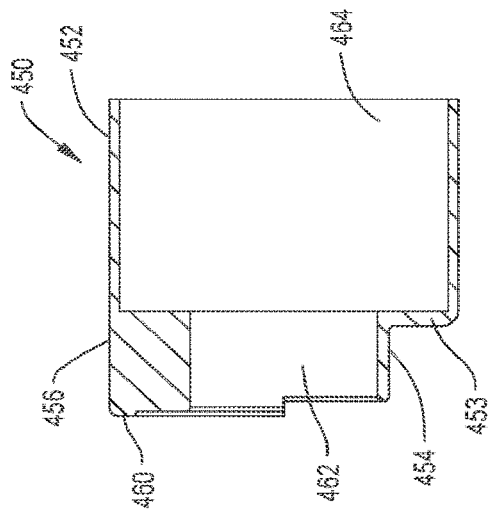
FIG. 19 is a cross sectional view of the thrust actuator taken along line 19-19 of FIG. 18.
Figure 17:
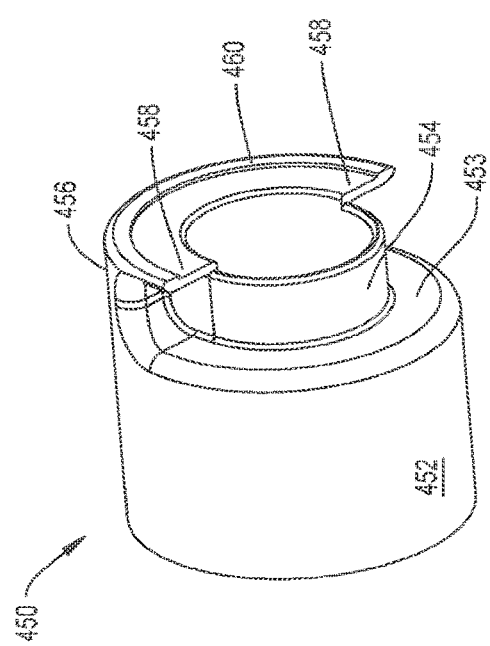
FIG. 17 is a perspective view of the thrust actuator of the wire driver.
Figure 25:
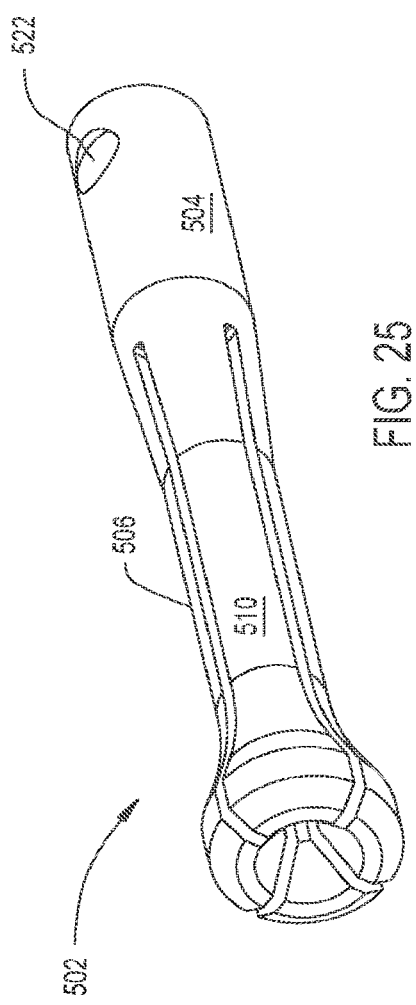
FIG. 25 is a perspective view of the collet of the wire driver.
Figure 26:
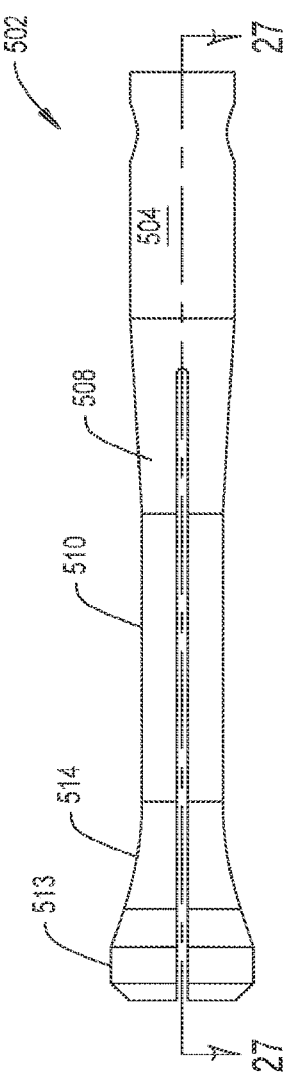
FIG. 26 is a side plane view of the collet.
Figure 27:
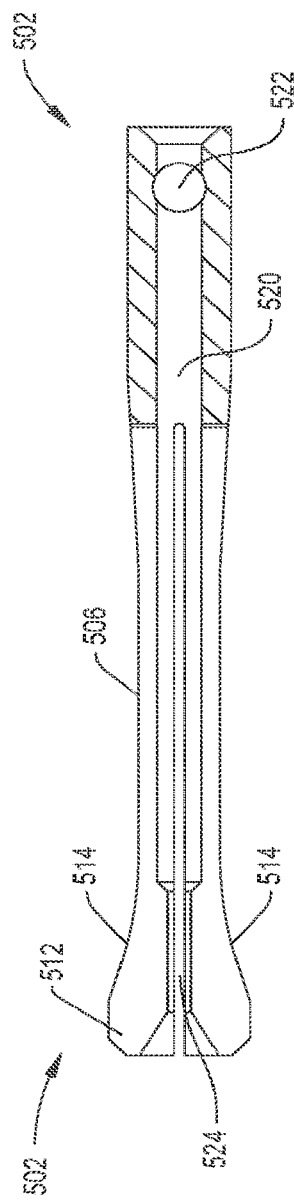
FIG. 27 is a cross sectional view of the collet taken along line 27-27 of FIG. 26.

An actuator 450, seen best in FIGS. 17-19, is disposed in the housing 84 to move longitudinally over the drive shaft torso 173. The actuator 450 has a head 452 that subtends most of the length of the actuator. Extending proximally rearward from head 452, the actuator 450 has a tube-shaped neck 454. Neck 454 has an outer diameter that is less than that of head 452. Actuator thus has an arcuately shaped, proximally directed step 453 that defines the transition from the head 452 to the neck 454.

A collar 456 extends radially outwardly from an arcuate section of the neck. Collar 456 extends around an arc that subtends approximately 160° of the total circumference of the neck. The outer diameter of collar 456 is equal to the outer diameter of head 452. At the proximal end of the actuator 450, tabs 458 extend arcuately outwardly from the opposed ends of collar 456. Each tab 458 is thus spaced proximally from the adjacent portion of the step 453. The actuator collar 458 is further shaped to have a rim 460 that extends arcuately around the whole of the proximally directed face of the collar. Rim 460 extends proximally rearward relative to the proximally directed face of the collar 450.

Two contiguous bores extend longitudinally through the actuator 450. A first bore, bore 462, extends distally from the proximal end of the actuator 450 through the neck 454 and, by extension, across the collar 456. The proximal end of bore 462 forms the proximal end opening into the actuator 450. Bore 462 has a diameter that allows the drive shaft torso 173 to freely rotate within the bore. The distal end of bore 462 opens into the second bore internal the actuator, bore 464. Bore 464 has a diameter greater than that of bore 462. Bore 464 forms the distal end opening into the actuator 450.

When wire driver 80 is assembled, the actuator 450 is disposed in housing bore 106. The collar rim 460 seats against the distally directed face of the curved step surface between bore 102 and 106 internal to the housing 84. The drive shaft torso 173 is seated in both of the actuator bores 462 and 464. The drive shaft torso 173 also extends forward of the actuator 450.

A thrust bearing 468, seen best in FIG. 6B, is disposed in actuator bore 464. Thrust bearing 468 consists of a washer like body and a number of individual ball bearings (individual components of the thrust bearing 468 not identified). The body is formed with a number of openings. A ball bearing is seated in each opening. The ball bearings extend both proximal rearwards to and distally forward of the body of the thrust bearing 468. The thrust bearing 468 seated in the actuator bore 464 so the ball bearings are disposed against the circular step internal to the actuator 450 that defines the transition between bore 462 and bore 464. One or more thrust washers or shims 470, three shown, also seen in FIG. 4B, are located in the actuator bore 464 forward of the thrust bearing 468. The drive shaft torso 173 extends through the thrust bearing 468 and the washers 470.

A spring retainer 474, now described by reference to FIGS. 20 and 21, is also disposed over the drive shaft torso 173 and disposed in actuator bore 464. The spring retainer 474 has an outer base 476 that is both planar and circular in shape. The outer diameter of the base 476 is dimensioned to facilitate the slip fitting of the spring retainer 474 in actuator bore 464. A ring-shaped boss 478 extends distally forward from the inner perimeter of the base 476. Not identified is the center opening through the boss 478. This opening has a diameter slightly greater than that of the shaft torso 173 so the spring retainer can move longitudinally over the drive shaft 166. Boss 478 is formed to have three equiangularly spaced apart recesses 480. Recesses 480 extend distally forward from the proximally directed face of the boss. Each recess 480 also extends radially outwardly from the inner center opening-defining perimeter of the boss 478. Between each pair or arcuately adjacent recesses 480 the spring retainer is formed to have a notch 482. Each notch 482 extends through the whole of the proximally to distal length through the boss.

Disposed inside the drive shaft 166 is a wedge 486 and a collet 502. The wedge 486, shown in detail in FIGS. 22-24, has a tubular shaped body 488. Wedge body 488 has a diameter that allows the body to seat in the center opening of the spring retainer 474. Three feet 490 extend radially outwardly from the proximal end of the body 488. Feet 490 are equiangularly spaced apart from each other. The components forming wire driver 80 are dimensioned so that each wedge foot 490 can pass through the one of the notches 482 formed in the spring retainer 474. The components are further dimensioned so that each wedge foot 490 can seat in one of the recesses 480 formed in the spring retainer 474. Between each foot 490, the wedge body 488 is formed to have a longitudinally extending indentation 492. One indentation 492 seen in each of FIGS. 22-24.

The wedge body 488 has a through bore 494 that extends proximally-to-distally through the body. The wedge body 488 is further formed so that the inner wall of the body that defines bore 494 has a taper 496 that extends proximally from the distal end of the body. Specifically, as the surface 496 extends proximally from the distal end of the body, the diameter of taper surface 496 decreases.

The collet 502, now described with reference to FIGS. 25-27A, is a single piece component formed from flexible material. The collet 502 has a tubular shaped base 504 that forms the most proximal end of the collet. Collet base 504 is designed to snuggly fit in bore 180 internal to the drive shaft 166. Four equiangularly spaced apart legs 506 extend distally forward of the base. Each leg 506 is formed to have a proximal section 508 and a distal section 510. Extending distally from the base, the outer surfaces of the leg proximal sections taper inwardly towards the center of the longitudinal axis through the collet 502. The outer surfaces of the leg distal sections 510 define a circle that, along the length of the leg distal sections, is generally constant. Generally, the outer surfaces of the legs define circles that have diameters less than the constant diameter section of bore 494 internal to the wedge 486.

Extending from the distal end of each leg 506 is a foot 512. Immediately distal to the leg distal section 510, each foot has an ankle surface 514. Each foot 512 is formed so that extending distally from the associated leg 506, the ankle surface 514 curves outwardly. Stated another way, ankle surfaces 514 are concave in shape. As a result of this curvature, the feet ankle surfaces 514 collectively define circles that have diameter greater than the diameter of the constant diameter portion of wedge bore 494. Distal to the ankle surface 514 the outer surface of each foot 512 has a section 513 that has a constant diameter (surface not identified). Each foot 512 further defines a toe 515. The toe 515 extends radially inwardly relative to the adjacent inner surface of the leg 506 from which the foot 512 extends.

Collet base 504 and legs 506 define a channel 520 that extends distally from the proximal end of the base 504. Collet base 504 is further formed to have two coaxial holes 522. Holes 522 are located forward of the proximal end of the base 504. Holes 522 are centered on an axis that intersects and is perpendicular to the longitudinal axis through the collet 502. Holes 522 each open into channel 520.

The distal end of channel 520 opens into a channel 524. Channel 524 is defined by the inner curved surfaces of the collet toes 515. Channel 524 has a diameter less than the diameter of channel 520. The effective diameter of channel 524 is slightly less than the diameter or the smallest diameter wire or pin wire driver 80 is intended to implant. More particularly, the diameter of channel 524 is such that when the small diameter pin or wire is manually inserted into the channel, the feet 512 will slightly flex outwardly to releasably hold the pin or wire in the collet 502.

When wire driver 80 is assembled, the spring retainer 474 is slip fitted over the torso 173 of the drive shaft 166. Wedge 486 is inserted into the drive shaft 166. More particularly, the wedge feet 490 are passed through grooves 184 into shaft slots 186. Owing to the dimensions of the components, the feet protrude radially outwardly from the shaft torso 173. Wedge feet 486 are moved proximally through the notches 482 in the spring retainer 474. The spring retainer 474 is rotated so that each foot 490 integral with the wedge 484 seats in one of the spring retainer recesses 480. Collet 502 is inserted in the wedge bore 494 so the proximal end of the collet base 504 extends proximally rearward from the wedge 484. More particularly the collet base 504 is positioned so that holes 522 integral with the collet base are placed in registration with holes 185 internal to the drive shaft 166. Pins 528, seen in FIG. 6A, that extend through drive shaft holes 185 and collet holes 522 hold the collet 502 fast to the drive shaft 166. Wedge 486 is mounted to the drive shaft 166 to both rotate in unison with the drive shaft and move longitudinally along the drive shaft.

A spring 532, best seen in FIG. 6A, normally holds the wedge 486 in the proximal most position so that wedge taper 496 is spaced proximally away from the ankle surfaces 514 of the collet feet 512. Spring 532 is a coil spring that is disposed over the torso 173 and head of drive shaft 166. The distal end of spring 532 abuts the proximally directed face of the drive shaft lip 176. The drive shaft lip 176 is thus the static surface against which the spring 532 abuts. The proximal end of spring 532 is disposed against the distally directed face of the base 476 of the spring retainer 474. The components forming the wire driver are configured so that spring 532 is in compression. The spring 532 thus holds the spring retainer 474 in the position in which the retainer is located in the proximal most position relative to the drive shaft head 174. By extension, the spring retainer 474 holds the wedge 486 in the proximal position of the wedge relative to the collet 502.

Figure 29:
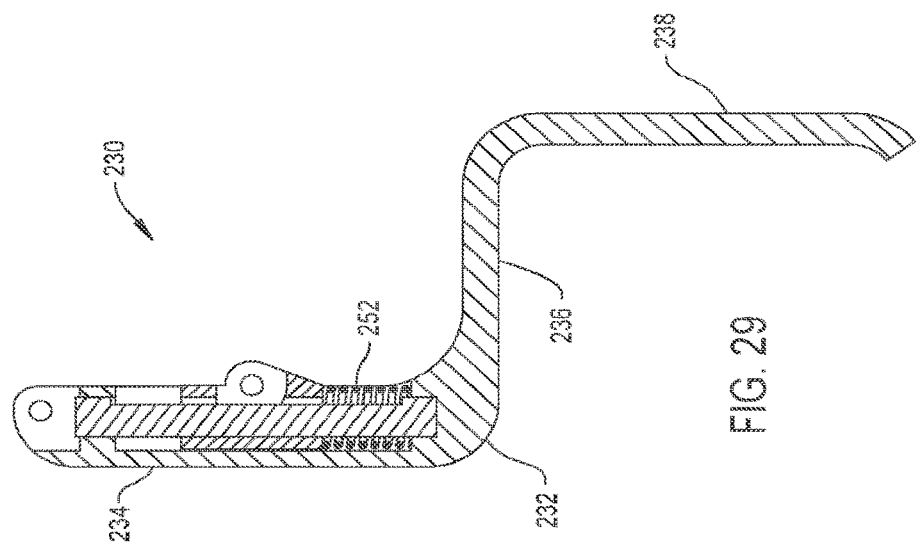
FIG. 29 is a cross sectional view of the lever.
Figure 28:
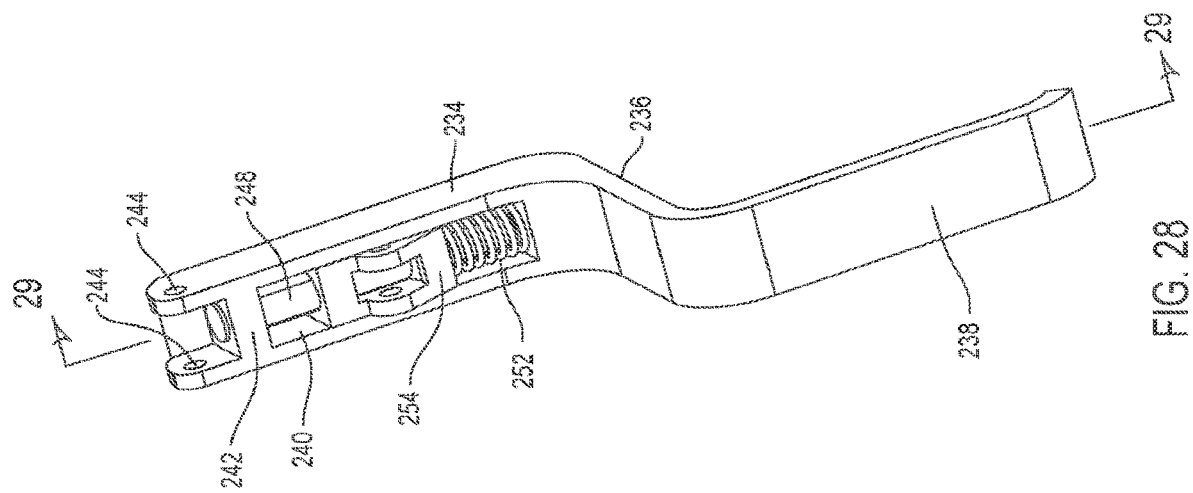
FIG. 28 is a perspective view of the lever and the components disposed in the lever of the wire driver.

Wire driver 80 includes a lever assembly 230 that, when actuated, advances the actuator 450. The advancement of the actuator 450 drives the wedge 486 against the collet ankle surfaces 512. Lever assembly 230 includes a bar-shaped lever 232 seen best in FIGS. 28 and 29. Lever 232 includes an upper section 234 that extends downwardly from wire driver housing 84. A middle section, section 236, extends proximally from upper section 234. In the depicted version of the invention, the level middle section 236 extends essentially perpendicularly from the upper section 234. A bottom section 238 extends downwardly from the middle section 236. Lever bottom section 238 forms the free end of lever 232.

Collectively, the components forming the wire driver 80 are constructed so that when the lever 232 is pivoted proximal, the lever bottom section with abut the finger 48 that protrudes forward from handgrip 46.

Lever 232 is further formed to have a groove 240 in the top section 234. Groove 240 extends from the top end of the lever, through the top section 234 and terminates above the middle section 238. Groove 240 opens inwardly from the proximally directed face of the lever top section 234. The groove 240 has a cross sectional shape, in planes perpendicular to the top-to-bottom longitudinal axis through the lever 232 top section 234, that is rectangular. Lever 232 is further formed to have a web 242 that extends side to side across the groove 240 to separate the groove into two sections (groove sections not identified). The lever 232 is formed so that web 242 is located a short distance, 1 to 3 cm, below the top of the lever. Web 242 is formed with a through hole (not identified) that runs top to bottom through the web. The lever 232 is formed to have two coaxial holes 244. Holes 244 are located above web 242. The holes 244 are located in the opposed sides of the lever 232. The holes 244 open into the section of groove 240 located above web 242.

A rod 248 is fixedly secured to the lever top section 234 so as to extend longitudinal through groove 240. Rod 248 is secured to the lever 232 to be spaced away from the inner surfaces of the lever that define the perimeter of groove 240. The base of rod 248 is secured in a closed end bore formed in the lever top section below groove 240 (bore not identified). The head of the rod 248 is seated in the through opening that extends through web 242. (Rod head not identified).

A spring 252 and a slide 254 are fitted over rod 248. The slide 254, seen in FIG. 30, includes a block 256. A bore 258 extends top to bottom through the block 256. Bore 258 is able to receive rod 248. The components forming the lever assembly 230 are constructed so that slide 254 seats over the rod 248 and is able to move freely along the rod. Two parallel and spaced apart tabs 258 extend outwardly from the opposed sides of slide block 256. Tabs 258 extend proximally from the slide block so as to extend beyond the proximally directed face of the lever top section 234. Each tab 258 is formed with a through hole 260. Through holes 260 are coaxial and are formed in the sections of the tabs 260 that project outwardly of the lever top section 234. The slide block 256 is formed with a window 262. Window 262 is located in the block between tabs 260. The slide 254 is formed so that window 262 opens into bore 258.

Spring 252 is a coil spring. The spring 252 is disposed around the rod 248 so as to be located between the surface of the lever top section from which the rod emerges and the undersurface of slide block 256.

A cam 268, seen best in FIG. 33, is pivotally attached to the slide 254. Cam 268 has an oval shaped body 270. The cam 270 thus has opposed parallel distally and proximally directed surfaces 272 and 273, respectively. In FIG. 33, only the edge of distally directed surface 272 is identified. A triangularly shaped tab 274 extends rearward from the proximally directed face 273. More particularly, the cam 268 is shaped so that the tab 274 has a relatively long surface that, extending from the body of the body extends upwardly and proximally. The tab 274 has a step surface 276, the edge of which is identified, that extends away from the proximally directed surface 273 of the cam body. Two through holes 278 and 280 extend side to side through the cam body 272. A first through hole, hole 278, extends through the body adjacent the bottom of the body. The second hole, hole 280, extends through the body adjacent the top of cam body 270.

When wire driver 80 is assembled, the cam 268 is positioned so that cam hole 278 is placed between and in registration with holes 260 integral with the slide 254. A pivot pin 282, identified in FIG. 6B, seated in the slide holes 260 and cam hole 280 pivotally holds the cam 268 to the slide 254.

Figure 31:
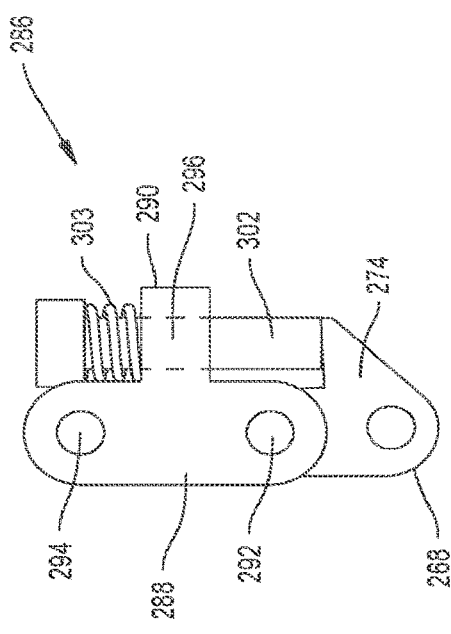
FIG. 31 is a side view of the cam assembly.
Figure 32:
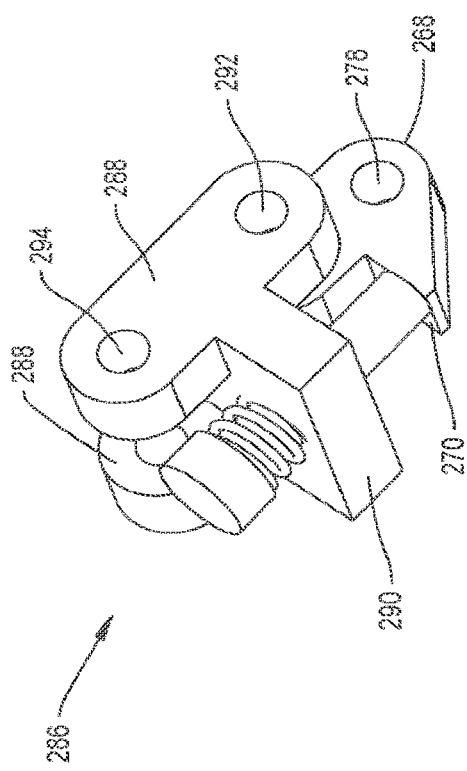
FIG. 32 is a perspective view of the cam assembly.

A cam link 286, seen best in FIGS. 31 and 32, pivotally connects cam 268 to legs 84 integral with the housing 84. The cam link 286 includes two parallel oval-shaped feet 288. Feet 288 are spaced apart from each other so cam 268 can seat between the feet. A web 290 extends between and connects the feet 288. Web 290 is planar in shape and is disposed in a plane that is perpendicular to the planes in which feet 288 are disposed. Web 290 projects proximally rearwardly beyond the feet 288.

Each foot 288 is formed with a through hole 292 that extend side to side through the foot. Through holes 292 are coaxial and located adjacent the lower end of the feet 288. Each foot 288 is formed with a hole 294 that is spaced away from hole 292. Holes 294 are coaxial and located immediately below the top end of the feet 288. A threaded bore 296 extends top to bottom through the section of the web 290 located proximal to the feet. Bore 296, without the threading, is shown in phantom in FIG. 31.

Upon assembly of wire driver 80, cam 268 is positioned between the feet 288 of the cam link 286. The cam 268 is positioned so that cam hole 280 is in registration with the feet through holes 292. A pin 298, identified in FIGS. 5 and 6B, extends through the cam hole 280 and cam link holes 292 to pivotally connect the cam 268 to the cam link 286. As a result of the joining of the cam 268 to the cam link 286, the cam step surface 276 is located below and spaced away from the web 290 integral with the cam link. A screw 302 is disposed in bore 296. The stem of screw 302 is positioned to be in close proximity to the cam step surface 276. A helical spring 303 is disposed between the head of the screw and the adjacent surface of web 290. Spring 303 is in compression, The opposed end of the cam link feet 288 are seated between legs 92 integral with housing 84. A pin 304, identified in FIGS. 5 and 6B, extends through the housing bores 118 and feet holes 292. Pin 304 pivotally secures the cam link 286 to the housing 84

An actuator link 306 extends between lever 232 and the thrust actuator 450. As seen best in FIG. 34, the actuator link 306 is generally an L-shaped, single-piece structure. The actuator link 306 has a cylindrical core 307 from which a horizontal section 308 extends distally forward. The horizontal section 308 is generally rectangular shape. A head 310 extends forward from the horizontal section 308. In a plane perpendicular to the plane of FIG. 3, the actuator head 310 has a width that is less than the width of the horizontal section 308. The head 310 is centered on the proximal to distal axis through the horizontal section. Head 310 is dimensioned to fit in the groove 240 formed in the lever 232.

A plate 314 extends vertically upward from core 307. Plate 314 is generally planar in shape. Plate 314 is formed so that two ears 316 extend upwardly from the opposed sides of the plate. Ears 316 are spaced apart from each. A lobe 318 is located at the end of each ear 316. Lobes 318 are parallel planes that are perpendicular to the both the plane of the link horizontal section 308. Lobes 318 are circular in shape. Collectively, the actuator link 306 and thrust actuator 450 are dimensioned so the actuator neck 454 can seat between the link ears 316 and the ear lobes 318 can seat in the spaces between step 453 and tabs 458 integral with the thrust actuator 450.

Actuator link 306 is formed with a bore 320 that extends side-to-side through the head 310. A bore 322 extends axially through the core 307.

When the wire driver 80 is assembled, the actuator link 306 is positioned so actuator bore 322 is aligned with bores 118 formed in the housing legs 118. Ear lobes 318 are seated between step 453 and tabs 458 integral with the thrust actuator 450. A pin 324, seen in FIGS. 5 and 6B, extends through the housing bores 118 and link bore 322 pivotally holds the actuator link 306 to the housing 84. A cap 325 is shown disposed over the free end of the shaft of pin 324. The link head 310 is seated in the groove 240 internal to the lever so the link bore 320 is in registration with holes 244 internal to the lever. A pin 326 that extends through lever holes 244 and link bore 320 pivotally holds link head 310, the distal end of the link 302 to the top of lever 232.

This invention is prepared for use by coupling the wire driver attachment 80 to the handpiece 42. Specifically, the attachment is fitted over head 51 integral with the handpiece barrel 52. Depending on the type of coupling components, this may require the rotation of lock collar 130 to ensure that housing pin 114 and lock collar pin 138 seat in the appropriate slots 53 formed in the handpiece head 51. As a consequence of the coupling of the attachment 80 to the handpiece 42, drive shaft 166 is coupled to the handpiece motor output shaft 56. The two shafts 56 and 166 are therefore able to rotate in unison.

At this time, the wire driver 80 is ready for use. At this time, lever 232 is not displaced. Spring 532 applies a force against the spring retainer 474 that holds the spring retainer in the proximal most position within housing bore 106. By extension, the spring retainer 474 holds the wedge 486 in the most proximal position. When the wedge 486 is so positioned, the distal end of the wedge is spaced away from the collet ankle surfaces 514. Wedge 480 therefore does not restrain the outward flexing of collet feet 512.

Also at this time, the free end of the stem of screw 302 is spaced away from the adjacent step surface 276 of cam 268.

A wire or a pin is then fitted to the wire driver 80 so the pin can be driven, rotated, by the wire driver. Short length pins and wires are inserted through the nose opening 198 into channel 524 and then channel 520 internal to the collet 520. Long length pins and wires may be inserted through handpiece tube 49 and the motor output shaft 56 through bore. From the motor output shaft 56 through bore the wire or pin extends through the wire driver drive shaft 166 and into the collet 502. More particularly, the wire or pin extends first into channel 520 and then into channel 524.

Regardless of how the wire or pin is inserted in the wire collet 502, owing to the dimensioning of the components, the wire or pin presses against the collet toes 515. FIG. 35A depicts the small diameter wire or pin 20 pressing against the collet toes 515. This force flexes the collet feet 512 outwardly. Thus the collet fleet 512 collectively compressively, removably hold the wire or pin to the collet 502. It should be understood that at least a portion of the wire or pin 20 being so held to the wire driver extends forward of nose 190 and therefore out of the wire driver 80. The wire or pin is now ready to be driven by the wire driver.

The process of driving the wire or pin starts with the surgeon pivoting the lever 232 so lever bottom section 238 is rotated towards the handgrip 46. This initial phase movement of the components forming the wire driver is the setup phase of the grasping process. The initial movement of the lever 232 causes the lever to rotate the horizontal section 308 of the actuator link 306 downwardly, clockwise in FIG. 5. This results in a simultaneous clockwise, generally distally directed movement of lever plate 314. The lever plate 314 applies a distal, forwardly directed, force against the thrust actuator 450. The force applied the lever plate 314 applies against the thrust actuator 450 overcomes the force spring 532 places on the actuator to hold the actuator in the proximal position. The thrust actuator 450 moves distally forward. This movement is transferred through the thrust bearing 468 and washers 470 to feet 490 integral with the wedge 480. Wedge 480 is thus pushed forward.

The forward movement of the wedge 480 causes the wedge tapered surface 496 to press against the collet ankle surfaces 514 as seen in FIG. 35A. The pressing of the ankle surfaces 514 urges the collet feet 512 inwardly. Collet toes 515 are forced against the wire or pin disposed between the toes. The force collet feet 512 apply against the wire or pin holds the wire is increased over the force that is applied when the wedge is spaced from the feet.

Simultaneously with the above movement, also during the setup phase movement of the wire driver 80, the pivoting of the lever 232 causes the lever to rotate cam 268 around pin 298. Simultaneously, there is some rotation of the cam link 286 around pin 304. In FIG. 5 both these movements would appear as clockwise rotations. Cam 268 rotates until cam step surface 276 rotates into contact with the base of screw 302. As a result of screw 302 abutting the cam 268, the continued rotation of the lever 232 causes the cam 268 and cam link 286 to rotate as a single-bar around pin 304. During this phase of pivoting of the lever 232, spring 252 prevents the downward movement of the slide 254.

Eventually the presence of the wire or pin blocks further radial inward movement of collet feet 512. By extension, further advancement of the wedge 486 is blocked. This means that further advancement of the thrust actuator 450 is likewise blocked. This means that the continued proximal pivoting of the lever 232 pivots the lever 232 and actuator link 306 as a single unit around pin 324. This movement is referred to as the "transition phase" movement of the lever 232. During this phase of movement of the lever 232, the cam 268 and cam link 286 pivot around pin 304. This causes the cam 268 to, in opposition to the force imposed by spring 252, push the slide 254 downwardly.

In addition to pushing slide 254 downwardly, the pivotally movement of cam 268 and cam link 286 cause the cam 268 to rotate around pin 282 and the cam link 286 to rotate around pin 304. These rotations would appear as clockwise rotations in FIG. 5. As a result of the movement of the cam 268, the distally directed surface 272 of the cam is urged against the rod 248. At this time the interface between rod 248 and cam surface 272 becomes the axis around which the cam 268, as a result of the continued pivoting of lever 232, rotates. Cam 268 thus functions as a rocker arm the rotational axis of which is the interface between rod 248 and cam surface 272. The rotation of the cam 268 around this axis is translated through pin 282 to a movement that forces the distal portion of the slide 254 against the adjacent surface of the rod 248. The slide 254 becomes friction locked against the rod 248.

The fact that the slide 254 is friction locked against the rod 248 means that in the next phase of the locking cycle, the slide 254 is static relative lever 232 and the cam 268 is static relative to the slide 254. At this time, the continued pivoting of the lever causes the wire driver to enter a final phase, a locking phase movement. At the start of this phase the lever 232, cam 268 and actuator link 306 function as a single rigid component. The pivoting of this sub assembly around the interface between rod 248 and cam surface 272, places a force of on the actuator 306. This force is transferred through the actuator to the wedge so as to increase the grasping force the collet feet 512 apply against the wire or the pin.

The locking phase movement ends with the lever bottom section 238 abutting finger 48 integral with the handpiece 42. Finger 42 thus functions as a stop that prevents the cam link 268 from being driven into an over center position.

Once the wire driver is in this grasping state, the wire driver is ready to drive the grasped wire or pin. The surgeon depresses the trigger 55 or 57 to actuate motor 54. The rotational moment of the motor output shaft is transferred to the wire driver drive shaft 166. Collet 502, it will be recalled, is connected to the drive shaft 166 for rotation with the drive shaft. Therefore, the rotation of the drive shaft results in the like rotation of the collet 502 as well as the wire or pin grasped between the collet feet 512. The surgeon applies an axial load on the exposed portion of the rotating wire or pin to drive this component into tissue.

The surgeon drives the wire or pin into tissue until nose 190 abuts the tissue. The surgeon then deactivates the handpiece motor 54 so as to stop the rotation of the wire or pin. Lever 232 is released. Since the cam link 268 was not driven into the over center position, the release of the finger force releases the potential energy stored in spring 252. Spring 252 pushes slide 254 upwardly. This results in the lever pivoting forward, in the counterclockwise direction in FIG. 5. This results in the actuator link 306 displacing the thrust actuator 450 proximally. The proximal movement of the thrust actuator 450 allows the spring 532 to release its potential energy. The expansion of spring 532 displaces the spring retainer 474 and, by extension, wedge 486 proximally. The translation of the wedge 486 away from the collet feet 512 results in the withdrawal of the force holding the feet against the wire or pin. The surgeon is thus free to move the wire driver 80 proximally. This movement exposes another section of the wire or pin between the bone and nose 190 by repeating the above-described process the surgeon can drive this newly exposed portion of the wire or pin into the bone.

Wire driver 80 of this invention is designed so that the lever assembly being a plural bar (at least two-bar) linkage, the lever assembly is able to displace the wedge over a relatively wide range of distance. This distance is typically at least 5 mm or more and to do so with the lever engaging in a relatively narrow arc pivot, 30° or less and, in preferred designs, 20° or less. The lever assembly 230 is able to so displace the wedge without having to set the position of the primary pivot point of the lever as a function of the wire/pin diameter. In addition to eliminating a step needed to configure the wire driver for use, this invention eliminates the possibility that the configuration step of setting the lever as a function of wire/pin diameter is performed incorrectly.

The wire driver of this invention is constructed so that, prior to the insertion of a wire or a pin in the collet 502, the wedge 486 is spaced proximally from the collet ankle surfaces 514. This means that the placement of a wire or a pin in the collet, regardless of the diameter of the wire or pin, does not result in a displacement of the wedge 486. Since the wedge 486 is not displaced this means the fitting of the wire or pin to the collet 232 does not result in the displacement of the lever 232. Thus, regardless of the diameter of the wire or pin fitted to the wire driver, the initial position of the lever 232 remains constant. This means that, regardless of the diameter of the wire or pin fitted to the wire driver, the same amount of effort is required to initial displace the lever in order to start the wire grasping process.

Further, owing to the curvature of ankle surface 514, the acute angle of surface 514 relative to a static axis parallel to the longitudinal axis through the collet 502 varies. More particularly, this angle increases as the distance from the collet legs 506 increases. A benefit of this feature of wire driver 80 of this invention is understood by reference to FIGS. 35A and 35B. As with the prior art, the extent to which the collet feet 512 are flexed away from the longitudinal axis through the collet is proportional to the diameter of the wire or pin being held by the collet 502. Owing to this, flexure the location where the wedge tapered surface 496 strikes the ankle surface 514 when the collet is used to hold a wide diameter wire or pin is closer to the collet legs 506 than when relative to the collet is used to hold a wire or pin of smaller diameter. Thus, the wire driver 50 of this invention is designed so that when a larger diameter wire or pin is being grasped, the wedge taper surface abuts adjacent ankle surfaces 514 that have a static, unflexed, acute angle that is relatively shallow. Here "relatively shallow" is understood to mean in comparison to when the wedge taper surface abuts the more distal portions of the ankle surfaces 514.

FIG. 35A illustrates the state of the wire driver when the collet 502 is used to hold the relatively small diameter wire or pin 22. When wedge 486 is advanced to grasp the wire or pin, the wedge must be advanced to a position in which wedge taper 496 abuts the ankles surfaces 514 at a location that is relatively close to the distal end of the collet 502. In a modeled version of the invention, this distance is 1.6 mm. Owing to the shape of the collet ankle surface and the fact that the collet feet are subjected to relatively small flexure, the acute angle of the ankle surfaces at this point of contact approximately 17°. When the same collet 502 is used to hold the larger diameter wire or pin 22, the collet feet are flexed outwardly more than when the small diameter wire or pin 20 is held. As seen in FIG. 35B, as a result of this increased flexure, when the wedge 486 is advanced to grasp the collet 502, tapered surface 496 strikes the ankle surfaces 514 at a location that is spaced further from the distal end of the collet. In the modeled version of the invention this distance is 4.8 mm. At this point of contact, the unflexed acute angle of ankle surface is less than in the example of FIG. 35A. Therefore, even though the flexure of the feet has increased this angle the overall angle is not significantly more than the example of FIG. 35B. In the depicted model, this angle is actually less than the angle of FIG. 35B. More specifically, in this model the angle is 12°.

This means that the amount of force the surgeon has to place on the wedge, apply through the lever 232, in opposition to the resistance imposed by the ankle surfaces 514, to complete the grasping of the wire or pin does not appreciably increase with the diameter of the wire or pin being grasped. Again, in the described version of the angle of contact between the wedge 486 and the collet 502 actually decreases when the diameter of the wire or pin being grasped increases. This means that for the same amount of longitudinal force applied by the wedge against the collet there is an increase in the radially inwardly directed grasping force. This increase in grasping force is desirable since, as the diameter of the wire or pin fitting to the wire driver increases, more grasping force is needed to hold the wire or pin fast for rotation with the drive shaft 166. Thus, a feature of this invention is that the amount of force the surgeon needs to apply to the lever in order to hold the wire or pin being driven fast to the drive shaft 166 does not appreciably increase with the diameter of the wire or pin.

Figure 36A:
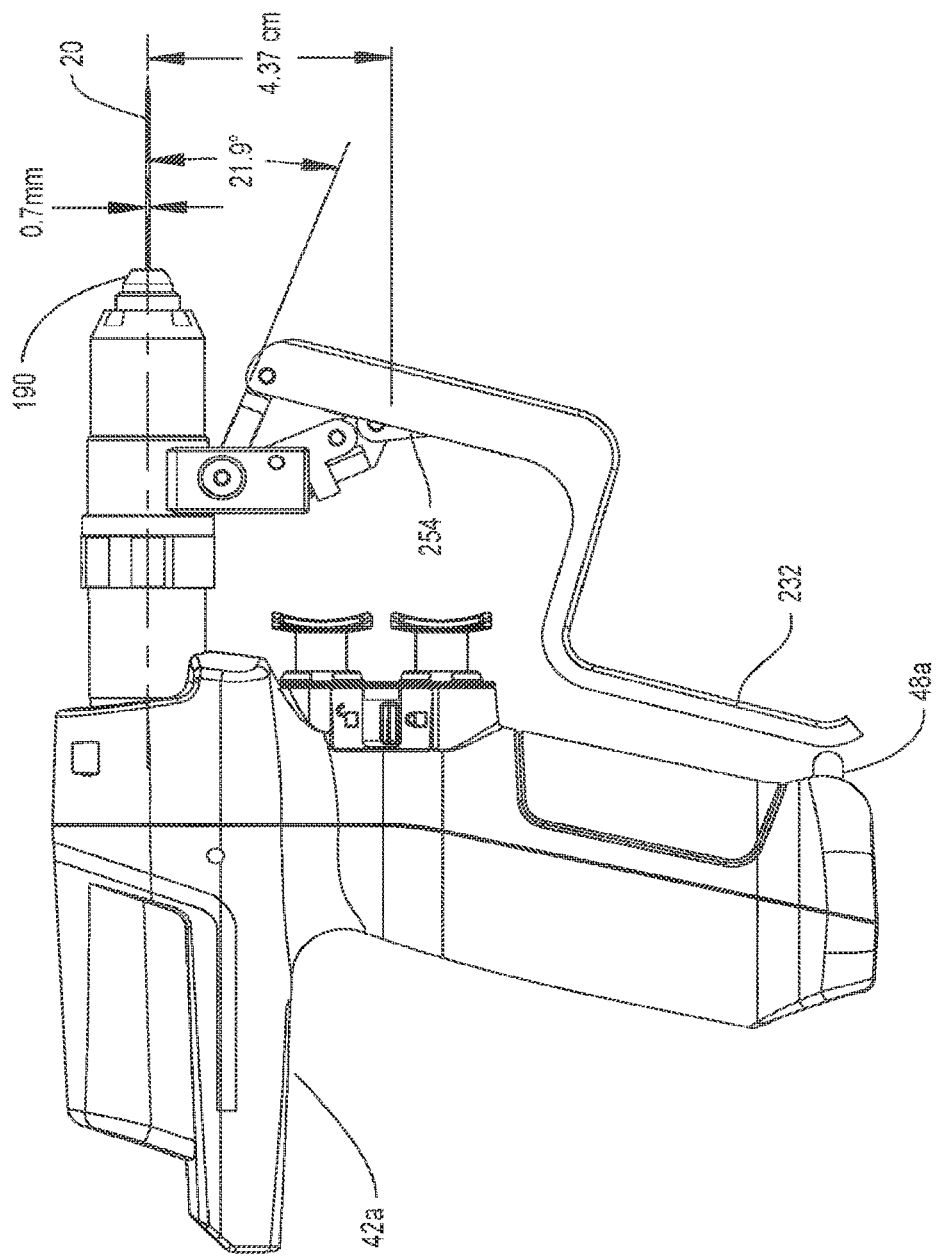
FIGS. 36A and 36B are side plan views depicting the movement of the components of the wire drive of this invention when, respectively, a small diameter wire and a large diameter wire, is fitted to the driver.
Figure 36B:
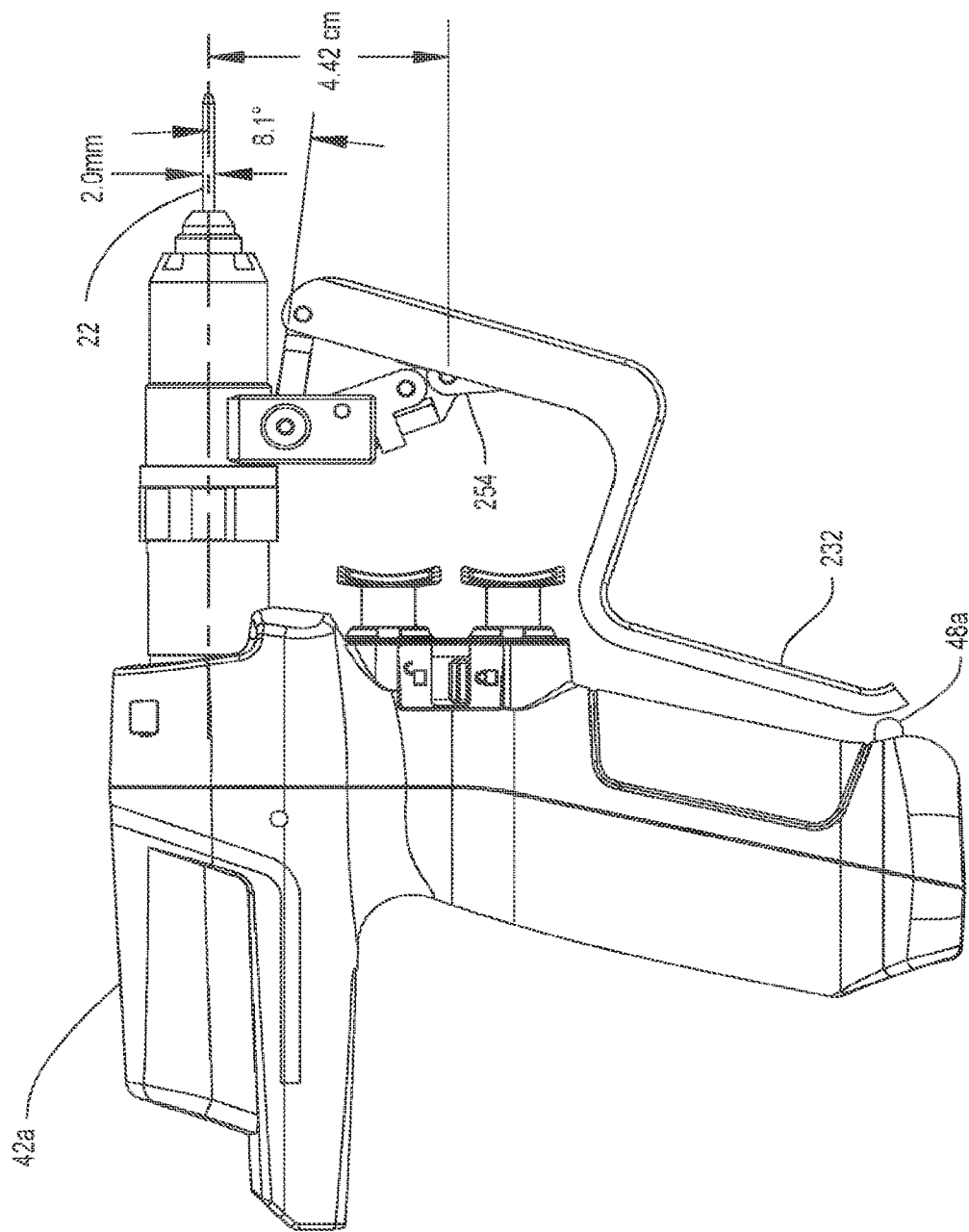

The wire driver of this invention is further designed so that the extent to which the slide is displaced downwardly along the rod is a function of the diameter or the wire or pin being grasped. FIG. 36A illustrates a wire driver 80 of this invention being used to grasp a wire 20 having a diameter of 0.7 mm. In FIGS. 36A and 36B, the wire driver 80 is shown connected to an alternative handpiece 42a. FIG. 36B is a model of the same wire driver 80 being used to grasp a wire 22 having a diameter of 2 mm. As seen in FIGS. 36A and 36B, the displacement of the slide 254 relative to the center of the nose 190, the center of the wire 20 or 22, is greater when the 2 mm wire 22 is being grasped in comparison to the displacement of the slide 254 when the 0.7 mm wire 20 is being grasped. As a consequence of this difference, the final position of the lever 232 is essentially constant, regardless or wire or pin diameter, as the wire drive enter the final portion of the locking phase. This means that independent of wire or pin diameter, the lever 232 at the end of the locking phase abuts finger 48a.

Collectively, the fact that the grasping force the wedge places on the collet feet increases with wire diameter and the fact that the final locking phase position of the lever is independent of wire or pin diameter means that this wire driver can be used to firmly grasp wires and pins that vary in diameter over a relatively large range of diameters. Here wide range of diameter is understood to mean a diameter such that the larges diameter pin that can be driven has a diameter at least two times the diameter of the smallest diameter and, preferably 2.5 times and still more preferably 3 times. This wire driver is able to so function without requiring the setting of a component to the specific diameter of the wire or pin being driven.

A further feature of this invention is that by setting the position of screw 302, the point in the process at which cam 268 and cam link 286 become a single rigid link can be selectively set. This allows for the adjustment of the force that is applied against the actuator 450. This, in turn, sets the force the collet feet apply against the wire or pin being grasped. It should be appreciated that the force applied against the actuator is proportional to the manual force applied against the lever. Thus, the setting of the screw 302 allows the surgeon to set the wire driver so that the lever can be lightly grasped so that in turn the wire or pin being held is only light grasped. Alternatively, the wire driver can be set so that, by applying a larger force to the lever, the wire or pin is held tighter to the drive shaft.

II. First Alternative Embodiment

Figure 37:
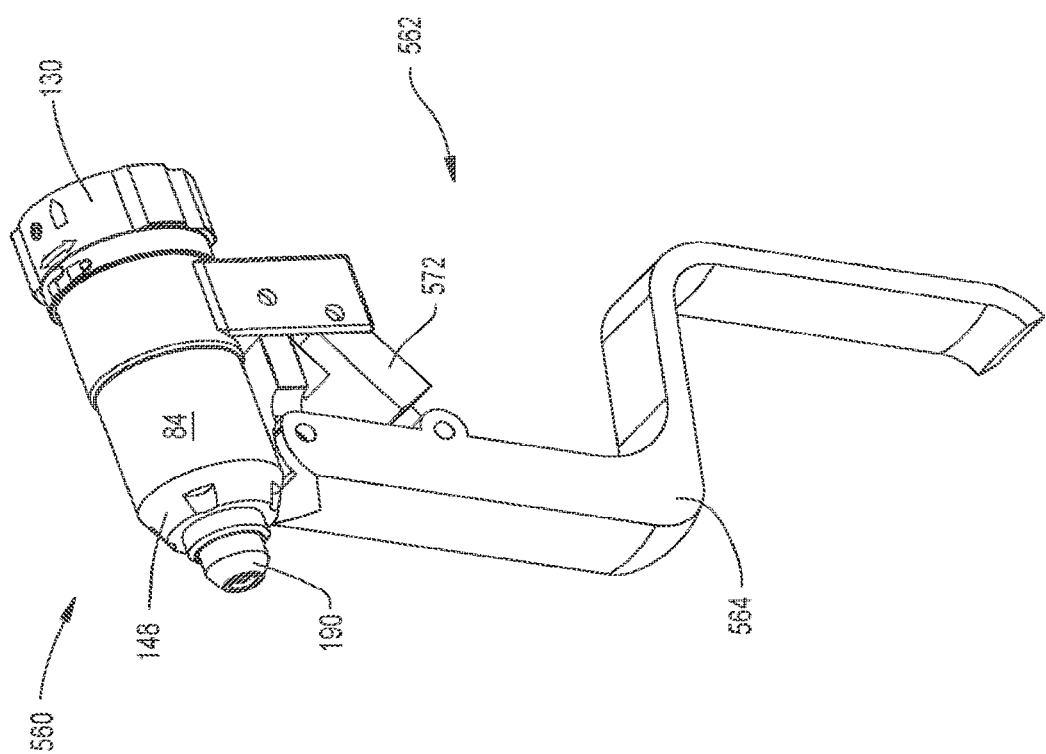
FIG. 37 is a perspective view of a first alternative wire driver of this invention.

FIGS. 37 and 387 depict an alternative wire driver 560 of this invention. Wire driver 560 has some of the same basic components of previously described wire driver 80. To avoid redundancy, the majority of these identical components are neither described not illustrated.

Wire driver 560 includes a lever assembly 562 different from lever assembly 270. Lever assembly 562 includes the previously described actuator link 306. Actuator link 306 is mounted to the legs 92 integral with housing 84 as described with respect to wire driver 80. A lever 564 pivots actuator link 306. Lever 564, like lever 232, has a top section that extends generally vertically downwardly from the housing 84 and middle section that extends perpendicularly and proximally away from the top section. Lever 564 also has a bottom section that extends perpendicularly downwardly from the middle section. The individual sections of lever 564 are not identified. Two parallel and spaced apart tabs 565, one identified, extend proximally outwardly from the lever top section.

Two links pivotally connect lever 564 to housing legs 92. One of these links is the horizontal section of actuator link 306. Head 310 of link 306 is seated in an opening 566 in the top of lever 564. A pivot pin 568 pivotally holds link head 310 the lever 564. Not identified are the opposed openings in the lever 564 in which the opposed ends of pin 568 are seated.

A toggle link 572 is the second link that extends between the housing legs 92 and lever 564. Toggle link 572 is shaped to have a head 574. The head 574 is shaped to fit between tabs 565 integral with lever 564. A base 576 extends proximally from head 574. Base 576 is wider in side-to-side width than head 574. Two parallel, spaced apart legs 578 extend proximally from the base 576. Legs 578 are formed with coaxial openings (not identified).

When wire driver 560 is assembled, link legs 578 are located between and pivotally mounted to housing legs 92. A pivot pin 582 that extends through housing leg openings 118 and the openings in the link legs 578, pivotally holds the toggle link 572 to the housing 84. Link head 574 is disposed between the tabs 565 integral with lever 564. A pin 584 extends through coaxial openings in the lever tabs 585 and link head 574 to pivotally hold link 572 to lever 564.

Wire driver 560 works in the same general manner as wire driver 80. The pivoting of lever 564 proximally results in the like pivoting of the actuator link 306 and the toggle link 572. In FIG. 37 this appears as the counterclockwise rotation of links 306 and 576. The pivoting of the actuator link 306 results in the distal movement of the wedge 486. The distal movement of the wedge 486 results in the wedge pushing the collet feet 512 towards each other. The wire driver thus enters the grasping state in which the collet tightly holds the inserted wire or pin to the drive shaft 166.

Wire driver 560, like wire driver 80, includes a lever assembly that is four-bar linkage. A difference between the two wire drivers 80 and 560 is that one of the links of driver 80 is includes a self-adjusting variable length link, collectively, slide 254, cam 268, and cam link 286. The equivalent link of wire driver 560 is the single rigid bar toggle link 572. Wire driver 560 has less parts and is easier to assembly than wire driver 80. Wire driver 560 can be an economical alternative to wire driver 80. This is especially the situation if the tool is to be used to drive wires or pins that have a relatively small range of diameters.

III. Second Alternative Embodiment

Figure 40:
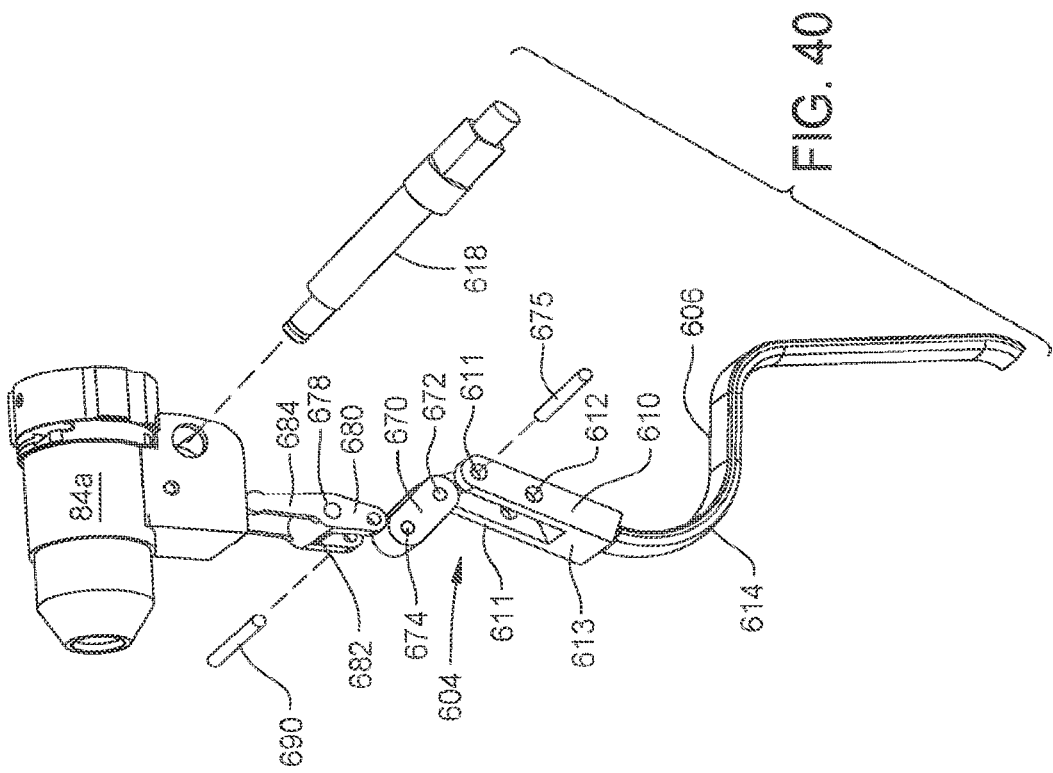
FIG. 40 is an exploded view of the wire driver of FIG. 39.

A second alternative wire driver 602 is now described by initial reference to FIGS. 39 and 40. Wire driver 602 includes the same basic internal components as wire drivers 80 and 560. Accordingly, these basic components are not redescribed.

Wire driver 602 includes a lever assembly 604. Lever assembly 604 includes a lever 606. Lever 606 includes a head 608. The lever head 608 includes two spaced apart parallel ears 610. Each ear 610 is formed with two through holes. A first through hole, hole 611, is located adjacent the top of each ear 610. A second through hole, hole 612, is located further from the tip. The ears extend downwardly to a base 613 also part of the head. A bent metal beam 614, also part of the lever 606, extends downwardly from head base 613. The beam 614 is shaped to immediately below the head, curve downwardly and proximally. The beam 614 then extends proximally so as to have a section that is generally parallel with the longitudinal axis of the wire driver housing 84a. At the end of the proximal section, the beam 614 curves downwardly. (Individual sections of the beam are not identified).

A pin 618, seen best in FIGS. 40 and 43, pivotally holds the lever between legs 92a of the housing 84a. The pivot pin 618 has a cylindrical leg 620. A cylindrical torso 622 extends away from the leg 620. The torso 622 has a diameter greater than that of the leg 620 and a longitudinal axis laterally offset from the longitudinal axis through the leg 620. The pin 618 has a cylindrical neck 624 that is located forward of the torso 622. Neck 624 has a diameter greater than that of the leg. The leg 620 and neck 624 of pin 618 are coaxial. The pin 618 has a head 626 located forward of the neck 624 and a nose 628 located forward of the head. In cross section, in planes perpendicular to the longitudinal axis of the neck 624, pin head 626 is square in shape. The pin head 626 does not project radially beyond the outer perimeter of the neck 624. Nose 628 is cylindrical in shape. Nose 628 is centered along a line that extends from the center of neck 624 and through the center of pin head 626. The outer perimeter of the nose 628 is recessed inwardly relative to the outer perimeter of the head 626.

Pin 618 is rotatably mounted between housing legs 92a. There are minor differences in the shapes of the openings within the legs as depicted in FIGS. 39 and 40 in comparison to FIGS. 41 and 42. One leg 92a has a circular opening, opening 630. Opening 630 is dimensioned to receive the leg 620 of the pin. A retaining ring 632 is disposed over the end of the pin leg 620 that projects out of the housing 84a. The opposed housing leg is formed with an opening 634. Opening 634 has contiguous inner and outer sections, sections not identified. The inner section is circular in cross section and dimensioned to receive pin neck 624. The outer section is square in cross section and extends outwardly beyond the inner section.

Figure 44:
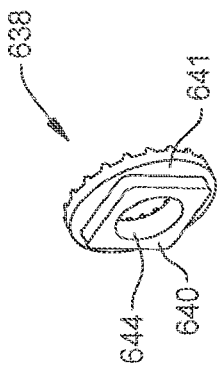
FIG. 44 is a perspective view of the inwardly directed portions of the lock ring of the assembly of FIG. 41.
Figure 45:
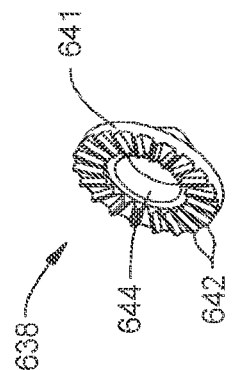
FIG. 45 is a perspective view of the outwardly directed portions of the lock ring of FIG. 44.

A lock ring 638, now described by reference to FIGS. 44 and 45, is disposed in the housing opening 634 around the pine neck 624. The lock ring 638 has a square shaped base 640. Ring base 640 is dimensioned to closely fit in housing the square portion of opening 634 internal to housing leg 92a. A circular head 641 extends outwardly from the base 640. Head 641 extends radially outwardly from the base 640. The lock ring is formed so that radially projecting and arcuately spaced apart teeth 642 extend outwardly from the exposed surface of the ring head 641. The lock ring 638 is further formed so as to have a center located through hole 644. Through hole 644 is dimensioned so that the pin neck 624 can seat and rotate in the hole 644.

A knob 646, seen best in FIGS. 46 and 47, is disposed over the pin head 626 and pin neck 628. The knob 646 is generally cylindrical in shape. The knob is formed to have a square shaped opening 648 that extends outwardly from the inner surface of the knob. More specifically, the components are dimensioned so that pin head 626 can be in a close sliding fit in opening 648. The knob 646 is further formed so to have teeth 650 that extend outwardly from the inner face of knob. Knob teeth 650 are dimensioned to mesh with lock ring teeth 642. Opening 648 opens into a bore 652 that extends axially through the knob 646. The knob 646 is formed so that bore 652 is cylindrical in shape and extends radially outwardly from opening 648. Bore 652 extends to the outer face of knob 646. Not identified are the indentations on the outer cylindrical surface of the knob that facilitate the finger grasping of the knob.

When wire driver 602 is assembled, the lever head 608 is positioned so that openings 611 are in registration with openings 630 and 634 of housing 84a. Pin 618 is inserted through housing opening 634, the lever openings 611 and the housing opening 630. Retaining ring 632 is fitted over pin leg 620 using a means not relevant to the present invention. Lock ring 638 is disposed between pin neck 624 and the portion of the housing 84a that defines opening 634. Knob 646 is sliding disposed around pin head 626. A coil spring 654 is disposed in bore 652 around the pin head 626 and nose 628. A washer shaped cap 656 is disposed over the end of the nose 628. The outer perimeter of cap 656 abuts the inner surface of the knob that defines bore 652. When cap 656 is in place, one end spring 654 is disposed in the step internal to knob 646 between opening 648 and bore 656. The opposed end of the spring 654 presses against cap 656. Spring 654 is thus in compression. Since the spring 654 is in compression, the spring places a force on the knob that hold the knob teeth 650 in engagement with the lock ring teeth 642. The force the spring 650 places on the knob 646 can be overcome by finger force.

A transfer link 670 is pivotally connected at one end to lever 606. Transfer link 670 is oval in shape. The transfer link is formed with two bores, bores 672 and 674 that extend side-to-side through the link. Bore 672 is located forward of the proximal end of the link 670. Bore 674 is located rearward of the distal end of the link 670. When wire driver 602 is assembled, the transfer link 670 is positioned so the link is disposed between lever ears 610 and bore 670 is in registration with holes 612 formed in the ears. A pin 675 that is seated in lever holes 612 and extends through link bore 670 pivotally connects the transfer link 670 to the lever head 608.

Lever assembly 604 also includes an actuator link 678 seen best in FIG. 40. The actuator link 678 includes a cylindrical core 682. Not identified is the through bore that extends end-to-end through the core 682. A leg 680 extends downwardly from the opposed ends of the core 682. Legs 680 are parallel and spaced apart from each other. Transfer link 670 and the actuator link 678 are collectively shaped so that the legs 680 seat adjacent the opposed sides of the transfer link. Not identified are the openings that extend side to side through the actuator legs 680.

Figure 48:
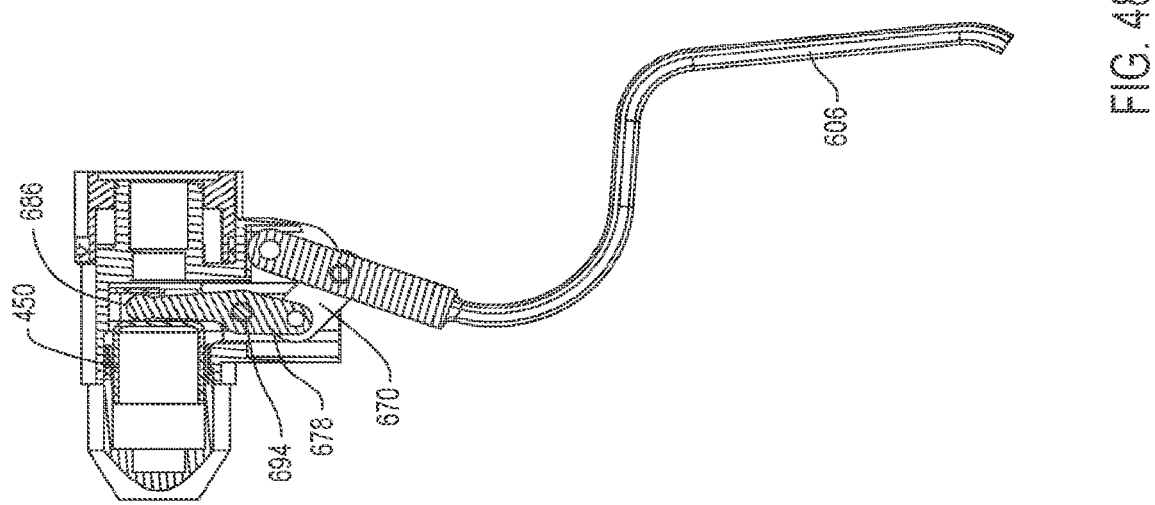
FIG. 48 is a cross sectional view of some of the components of the wire driver of FIG. 39 when the wire driver is in the release state.

Actuator link 678 also includes two parallel, spaced apart ears 684. Each ear 684 extends from a separate end of the core 680. Each ear 684 is coplanar with the adjacent leg 680. A circular lobe 686, identified in FIGS. 48 and 49, extends outwardly from the free end of each ear 684.

When the wire driver 602 is assembled, a pin 694 extends through coaxial openings in the housing legs 92a and through the bore that extends through actuator core 682. (Housing leg openings not identified). The link legs 680 are disposed around the transfer link 670. A pin 690 extends through openings in link legs 680 and the bore 674 in the transfer link. Pin 690 thus pivotally connects the actuator link 678 to the transfer link 670. The ear lobes 686 integral with the actuator seat against the actuator 450 internal to the housing 84a in manner similar to how lobes 318 seat against the actuator.

Figure 49:
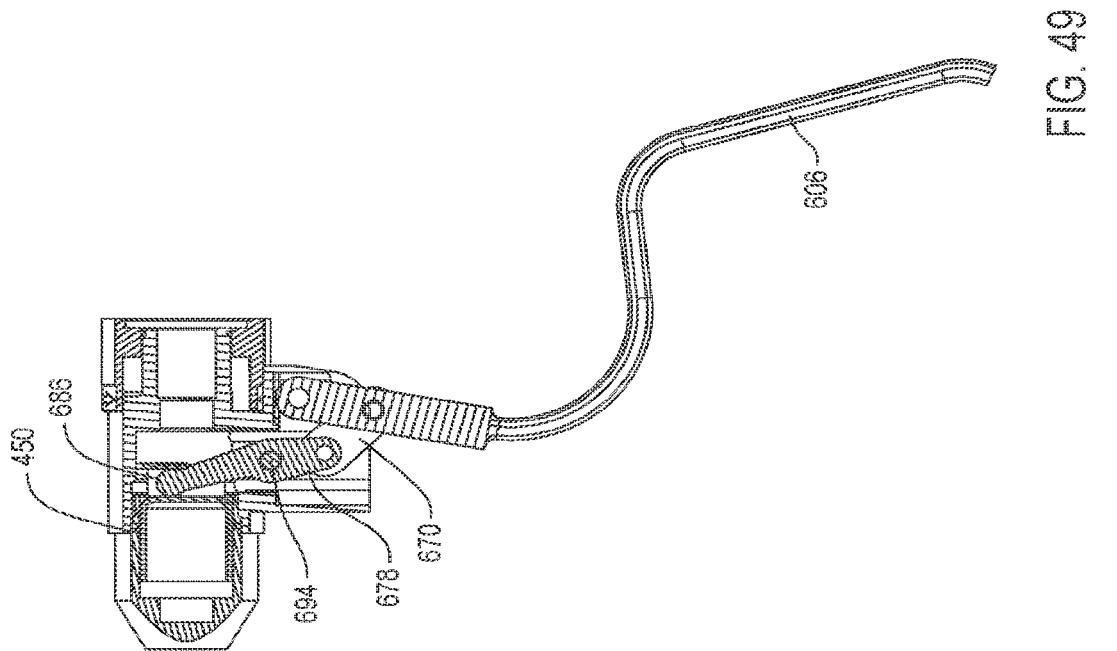
FIG. 49 is a cross section view of some of the components internal to the wire driver when the wire drive is in the grasping state.

Wire driver 602 is used a manner similar to that of the previously described wire drivers 80 and 560. Lever 606 is pivoted proximally. This results in the proximal rotation of the transfer link 670 with the lever 606. The displacement of the transfer link results in the pivoting of the actuator link 678. This movement in FIG. 48 would appear as the counterclockwise rotation of the actuator link 678. This movement of the actuator link 678 results in the forward, distal displacement of the actuator 45a as seen in FIG. 49. The actuator 450 forces the wedge against the collet feet so the feet securely hold the wire or pin to the drive shaft. To minimize drawing complexity, the wedge, the collet and the drive shaft are not seen in FIGS. 47 and 48

Wire driver 602 of this embodiment of the invention is further constructed so that the rotation of pin 618 results in the shifting of the position of the pin torso 622 relative to the housing 84a. The movement of the pin torso 622 results in a like shifting of the location of the pivot axis around which the actuator link 678 rotates. This axis positioning can thus be set as a function of the diameter of the wire or pin that is to be driven by the wire driver 602.

A benefit of this embodiment of the invention over the first two embodiments of the invention is that at rest position of the lever 606 is spaced closer to the proximal end of the wire driver housing. By extension, this means the lever when at rest is closer to the handgrip 46 of the handpiece 42. This reduces the extent to which the surgeon is required to extend his/her fingers in order to actuate the lever assembly. For some surgeons, especially those with relatively small hands, this can be ergonomically desirable feature.

IV. Alternative Collet

FIG. 50 depicts a leg 506 and a foot 512a of an alternative collet 502a of this invention. Collet 502a has the same base and legs as collet 502 of FIG. 27. Accordingly, these components are not redescribed. Collet 502a has a foot 512a with the previously described toe 515. Collet foot 512a has an ankle surface 517. Ankle surface 517 curves outwardly and distally away from the distal section 510 of the associated collet leg distal section 510. More particularly the ankle surfaces 517 of collet 502 are convex in shape. In cross section in planes intersecting the longitudinal axis through the collet 502a, ankle surfaces 517 define a slice section of a circle.

Collet 502a of this invention can be employed with any of the previously discussed wire drivers. An advantage of collet 502a is understood by reference to FIGS. 51 and 52. FIG. 51 depicts when collet 502a is employed to grasp the small diameter wire or pin 20. As described before, when the small diameter wire or pin 20 is being grasped there is minimal deflection of the collet feet 512a away from the longitudinal axis through the collet. When wedge 486 is advanced to increase the grasping force applied against the wire or pin 20, the wedge has to be advanced a relatively long distance. Stated another way the wedge is advanced to a location that relatively short distance from the distal ends of the collet feet 512a. As a consequence of the advancement of the wedge 486, wedge tapered surface 496 abuts the outwardly curved collet ankle surfaces 517. The wedge tapered surface 496 and a tangent line from where on an ankle surface the wedge makes this contact is at a given angle, arbitrarily angle α.

Figure 52:
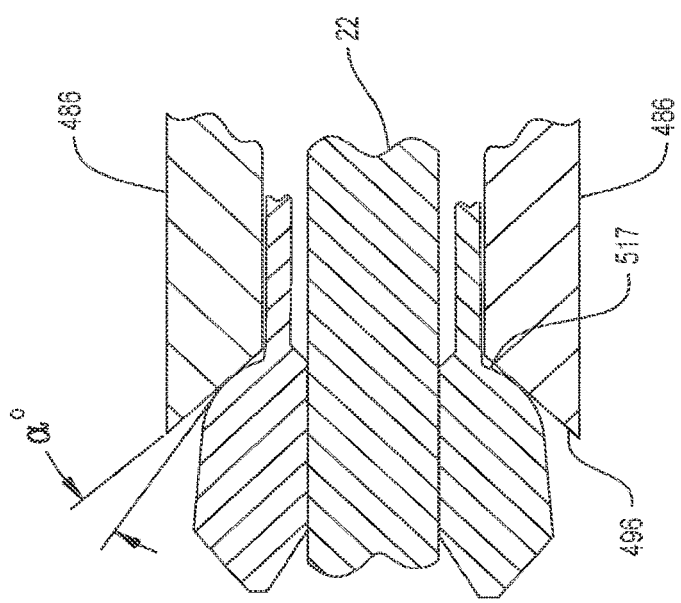
FIG. 52 is a cross sectional view when the collet of FIG. 50 grasping a large diameter wire or pin.

FIG. 52 depicts when the collet 502a is used to grasp a wide diameter wire or pin 22. When such a wire or pin 22 is being grasped, the collet feet 512a are deflected further away from the longitudinal axis of the collet than when the narrow diameter wire or pin is being grasped. While not seen this further deflection may include the bending or flexing of the collet feet such as that the angle between the longitudinal axis of the collet and the longitudinal axes through the collet feet increases. All other factors being equal, this angle should be the same for each of the collet feet 512a. In either case, the movement of the collet feet displaces the ankle surfaces 517 proximally. This proximal movement is the result of either the lateral and/or rotational movement of the collet feet 512a.

Consequently, when the wedge 486 is advanced to increase the grasping force the wire driver applies to a large diameter wire or pin 22, the wedge tapered surface 496 abuts the angle surfaces 517 at a location along that is spaced further from the distal end of the collet feet 512a than when the smaller diameter wire or pin 20 is being grasped. However, as when the small diameter wire or pin 20 is being grasped, the geometry of the ring of contact is the same, the planar tapered surface 496 of the wedge abuts a line around the spherically shaped anchor surface 517. Thus in the cross sectional plane that intersects the longitudinal axis of the collet, the angle between wedge tapered surface 496 and the tangent line from ankle surface 517 to where the contact made is identical, angle α.

This means that even though the collet feet 512a may move outwardly when a larger diameter wire or pin 22 is being driven by a wire driver of this invention, this shift in position of the collet feet do not reduce the mechanical advantage of the movement of the wedge 486 against the collet feet 512a.

V. Alternative Wedges

Figure 53A:
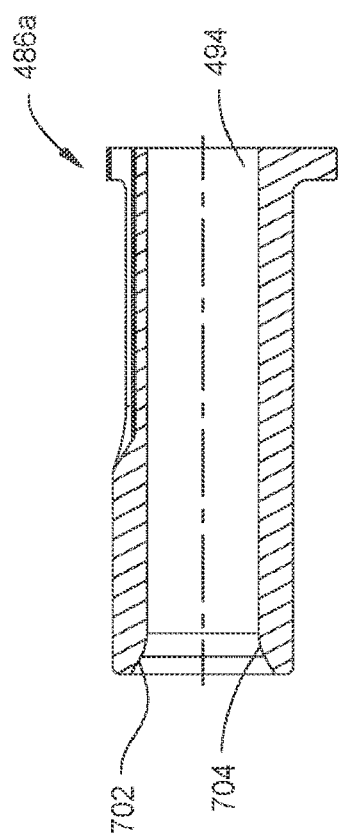
FIGS. 53A, and 53B are cross sectional views of alternative wedges of this invention.

FIG. 53A illustrates an alternative wedge 486a of this invention. Wedge 486a is similar to the first described wedge 486. A difference between the two wedges is the geometry of the tapered surfaces that defining the distal end opening into bore 494. Wedge 486a has a first inner surface 702 which is the most distal of the two inner surfaces. Inner surface 702 has a linear taper. Proximal to surface 702, wedge 486a has a second inner surface, inner surface 704. Surface 704 while being tapered, is curved. Thus surface 704 functions as a curved transition surface between surface 702 and the constant diameter inner surface of the wedge 486a that defines bore 494.

Figure 53B:
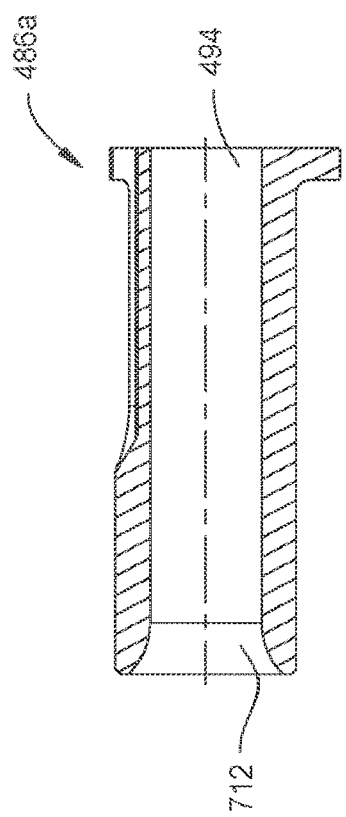

FIG. 53B depicts a second alternative wedge, wedge 486b. Wedge 486b has a single tapered inner surface, surface 712, that extending from the distal end of the wedge extends inwardly towards the longitudinal center of the wedge. Surface 712 is curved. More particularly, wedge 486b is formed with a convex curvature. Thus, as surface 712 extends proximally towards the surface of the wedge that defines bore 494, surface curves inwardly.

A benefit of wedges 486a and 486b of this invention is seen by reference to FIG. 54. In this Figure the wire or pin being grasped by the collet 502 is not shown for ease of illustration. In FIG. 54 inner surface 712 of wedge 486b is seen pressing against the curved ankle surfaces 514 of collet 502. Since this is a curve surface-against-curved surface abutment, the contact between the two surfaces 514 and 712 is around a relatively narrow length circle. Theoretically, this circle has a proximal to distal length of a single point.

A benefit of this band of contact being so narrow is that the frictional interface between the surfaces is likewise relatively narrow. This means that when the wire driver is moved from the grasping state back to the release state, only a relatively small amount of force needs to be applied in order to break the frictional bond that between the inner surface of the wedge and the underlying ankle surfaces of the collet.

It should be understood that for this feature to function well the radii of the inner surface of the wedge and of the collet ankle surfaces should be less than radius of curvature of the collet ankle surfaces 514.

Wedges 486a and 486b of this invention may also be used in combination with collet 502a.

VI. Alternative Linkages

Figure 55:
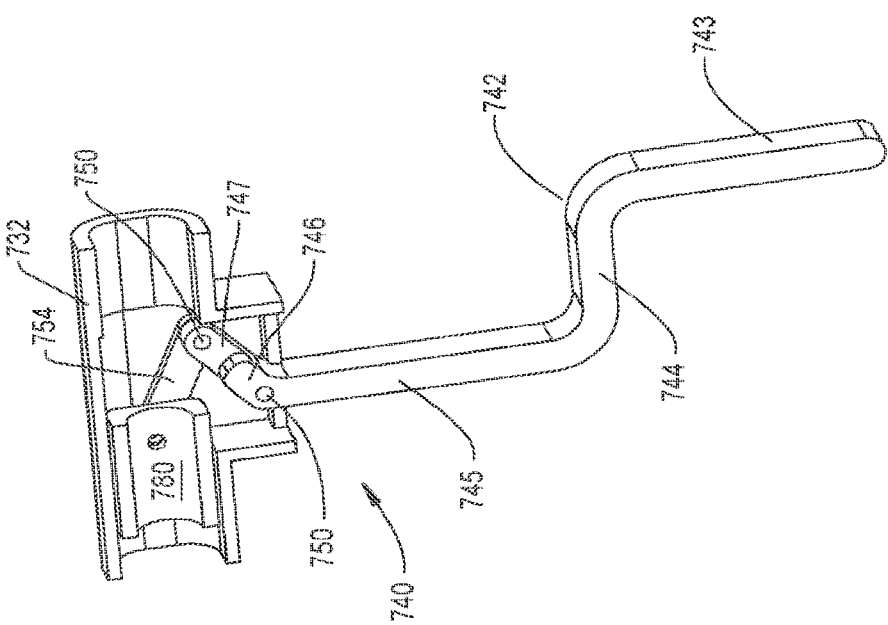
FIG. 55 is a break away depiction of components of a two-bar linkage assembly of this invention.

FIG. 55 depicts the components of a two-bar linkage assembly 740 of this invention. The wire driver with which assembly 740 is integral includes a housing 732. A thrust actuator 780 is slidably mounted in the housing 732. Not shown are the drive shaft or the collet internal to the housing as these are the same as the previously described versions of these components. The thrust actuator 780 abuts one of the previously described wedges 486, 486a or 486b of this invention. Again, for ease of illustrate the wedge is not shown.

Linkage assembly 740 includes a lever 742. Lever 742 has a generally vertically oriented bottom section 743, a middle section 744 that extends distally forward from the bottom section and top section 745 that extends upwardly from the middle section 744. In the illustrated version of the invention, lever bottom and top sections, 743 and 745, respectively are parallel. The lever also has a head 746 that extends upwardly and proximally away from the top of the tip section 745. A nose 747 extends upwardly and proximally away from the head 746. Nose 747 has a side-to-side depth, a thickness, that is less than the depth of the rest of the lever. The lever 742 is pivotally connected to the housing 732 by a pin 750. Pin 750 extends through the portion of the lever where the head 746 extends away from the top section 745.

A link 754 extends between the lever 742 and the thrust actuator 780. One end of link 754 is pivotally connected to the free end of the lever nose 747. A pin 750 pivotally connects link 754 to nose 747. The opposed end of link 754 is pivotally mounted connected to the outer surface of the thrust actuator 780 (connecting component).

To move a wire driver with linkage assembly 740 to the grasping state, the lever bottom section 743 is pivoted proximally, counterclockwise in FIG. 54. The like counterclockwise rotation of the lever nose 747 urges the link 754 forward. The forward movement of the link results a like movement of the thrust actuator 780. The thrust actuator 780 thus displaces the wedge forward so the wedge forces the collet feet 512 or 512a into the grasping position.

Figure 56:
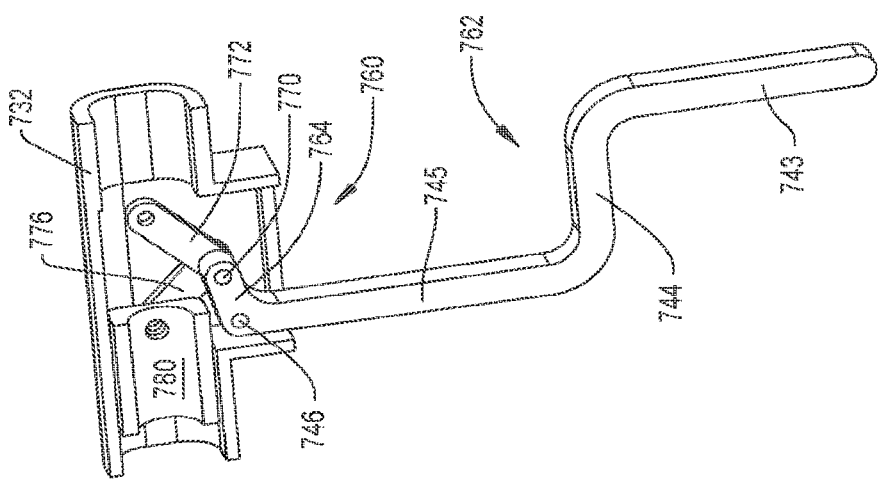
FIG. 56 is a break away depiction of components of a three-bar linkage assembly of this invention.

FIG. 56 depicts how a wire driver of this invention may be provided with a three-bar linkage assembly 760. The wire driver depicted in this Figure includes the housing 732 and thrust actuator 780 of the version of the invention depicted in FIG. 55.

Linkage assembly 760 includes a lever 762. Lever 762 includes the bottom section 743, the middle section 744 and the top section 745 of lever 742. A head 764 extends proximally and distally away from the free end of the lever top section 745. A pin 766 pivotally holds lever 762 to the housing 732. The pin 766 extends through the portion of the lever 762 wherein the head 764 extends away from the top section 745.

Linkage assembly 760 also includes first and second links 772 and 776, respectively. The proximal end of link 772 is pivotally connected to the housing 732, (connecting component not shown). This connection is at a located spaced proximal to the free end of lever head 764. The distal end the second link 776 is pivotally connected to the thrust actuator 780, (connecting component not shown). A pin 770 extends from the free end of the lever head 764. Not shown is where the pin extends through the distal end of the first link 772 and the proximal end of the second link 776. Pin 770 thus pivotally connects the links 772 and 776 to the lever 762.

To place a wire driver with linkage assembly 760 in the grasping state, lever 762 is pivoted proximally, counterclockwise in FIG. 56. The resultant counterclockwise movement of the lever head 764 pivots the first and second links 772 and 776, respectively. More specifically the links are pivoted to moving the position as depicted in FIG. 56 wherein the links are angled relative to each other towards a position in which the links longitudinally align with each other. This pivoting movement of the links 772 and 776, urges the distal end of the second link 776 forward. This results in a like forward movement of the thrust actuator 780. As with the version of the invention described with respect to FIG. 55, the movement of the thrust actuator displaces the wedge so as to urge the collet feet 512 or 512a into their grasping position.

VII. Alternative Embodiments

The above is directed to specific versions of the wire drier of this invention. Other wire drivers of this invention may have features different from what has been described. For example, as mentioned above an alternative wire driver of this invention may be constructed so the wire/pin grasping components are built into the handpiece of the wire driver.

Not all versions of the invention may include all the features of this invention. For example, a wire driver of this invention may include the plural bar lever or link assembly and not include the collet or wedge of this invention. A wire driver with a single-bar linkage may include the inventive collet or the inventive wedge of this invention.

In the described version of the invention the collet has four legs and complementary feet. In an alternative version of the invention, the collet may have fewer or more legs and feet.

In an alternative version of the invention, the wire driver may built into a handpiece that has a shape different from the illustrated pistol shaped handpiece.

The shapes of other features of the handpiece of this invention may likewise vary from what is illustrated. For example in versions of the invention wherein the angle of the outside of the collet ankle surface varies along the length of the surface, the surface may not always be curved. In some versions of the invention this surface may consist of plural planar surfaces. Each of these surfaces are at different angle relative to the longitudinal axis through the collet.

In some versions of the invention, the positions of the surfaces on the wedge and collet to maintain or increase the mechanical advantage when the collet feet are displaced may be reversed. Thus, in some versions of the invention, the wedge tapered surface may be a convexly curved surface and the collet ankle surfaces are planner. Alternatively, in some versions of the invention both the surface of the wedge and the ankle surfaces may be curved. These surfaces may have the same or different radii of curvature.

The features of the wire drive of this invention may be employed independently of each other. For example, there is no requirement that all versions of this invention include the plural bar linkage. Likewise, there is no requirement that in all versions of this invention include the collet with the ankle surface that has an angle that varies along the length of the ankle. Likewise, the different features of this invention may be combined. Thus, one or more the inventive features of the collet of this invention may be employed with one of the plural bar linkages other than the four-bar linkage.

In some versions of the invention a coating is applied over one or both of tapered surface 496 of the wedge and ankle surfaces 514 of the collet. This coating is applied to reduce the friction between the wedge 486 and the collet 502. This friction can be especially pronounced when the wire driver is employed to grasp a relatively large dimeter wire or pin. When the wire driver is employed for this purpose, the collet feet tend to extend out radially more than when wire driver is employed to grasp a smaller diameter wire or pin.

One reason it is desirable to reduce the friction between the wedge and collet 502 is to reduce the force required to advance the wedge 486 over the collet ankle surfaces 514. This is the movement of the wedge 486 over the ankle surfaces that occurs when the wedge is advanced distally forward in order to grasp, clamp, the collet toes 515 over the underlying wire or pin. A second reason this coating is applied concerns what occurs when the lever 230, 564 or 606 is released to result in a like release of the collet from the grasping state around the wire or pin. Spring 532 is the component of the assembly that, working against the spring retainer 474 urges the wedge away from the grasping position. The presence of the low friction coating on the wedge tapered surface 496 and/or collet ankle surfaces 514 reduces the force spring 532 needs to output to move the wedge away from the collet ankle surfaces. Minimizing the force spring 532 needs to output to function makes it possible to provide a wire driver with a weaker spring 532 than would otherwise be required. A benefit of providing a weak spring for spring 532 means that the surgeon needs to apply less force to the lever 230, 564, or 606 in opposition to the force the spring 532 places on the spring retainer 474 to force the wedge 486 into the grasping position over the collet 502.

The low friction coating that can be applied over one or both of the wedge tapered surface 496 or collet ankle surfaces 514 are Teflon; a nickel boron coating; or a boron-aluminum magnesium coating.

Not all versions of the invention may include all the features of the invention. For example, a plural bar version of this invention may not include the collet with ankle surfaces that are curved. The collet with the curved ankle surfaces of this invention may be incorporated into a wire drive that has a one-bar lever assembly for advancing the actuator.

In some versions of the invention it may be desirable to shape the wedge so that the inner surface of the wedge that presses against the collet feet has a concave curvature.

In versions of the invention wherein the stop that limits lever movement is present, the stop may not always extend from the handpiece. In some versions of the invention, the stop may be mounted to the housing that contains the linkage assembly. In these versions of the invention, the stop may be positioned to abut one of the links of the linkage assembly other than the lever.

In some versions of the invention, the stop that limits lever movement may be eliminated. In these versions of the invention it may be possible to drive one of the links of the linkage assembly into an over-center position. This would result in the hands-free locking of the wire driver in the grasping position. In these versions of the invention it may be necessary to provide a release lever separate from the grasping lever to force the wire driver from the grasping state to the release state.

Accordingly, it is an object of the appended claims to cover all such variations and modifications that come within the true spirit and scope of this invention.

What is claimed is:

1. A wire driver, said wire driver including:
a rotating drive shaft extending along a longitudinal axis and having a bore extending therein;
a collet extending axially between a proximal end and a distal end, said proximal end is disposed in the bore of the drive shaft and the collet being held fast to the drive shaft for unitary rotational and axial movement therewith and thus coupled to said drive shaft to rotate with said drive shaft, said collet having at said distal end a plurality of feet that are positioned to surround a wire or pin adapted to be driven into living tissue, said plurality of feet are radially moveable relative to the wire or pin so as to selectively grasp the wire or pin so the wire or pin rotates with the drive shaft, wherein, each foot of said feet has an outwardly located curved ankle surface having one of a concave profile and a convex profile and the one of the concave profile and the convex profile being radiused such that the curved ankle surface extends distally forward from a proximal portion of the collet, and curves outwardly away from the proximal portion; and
a wedge disposed over said collet and at least in part inside the bore of the drive shaft and the wedge being connected to the drive shaft to rotate in unison with the drive shaft and in selective engagement with the curved ankle surfaces and is moveable longitudinally relative to the drive shaft and said collet feet to have a grasping position in which said wedge surrounds and bears against the feet to cause the feet to grasp the wire or pin for rotation with said collet and a release position in which said wedge is spaced from said collet feet so the feet are released from grasping against the wire or pin; wherein said wedge is formed to have an inner surface that defines an open distal end of said wedge, the inner surface being tapered such that extending proximally from the distal end of said collet the inner surface tapers inwardly and a diameter of the tapered inner surface decreases proximally, and said wedge is disposed over said collet so that when said wedge is in the grasping position, the inwardly tapered inner surface of said wedge abuts the curved ankle surface of said collet feet, further wherein the curved ankle surface presents an angle of contact against the wedge at a point of contact therebetween with the angle of contact increasing with increased axial displacement of the wedge relative to the collet;
a housing containing said drive shaft, said collet and said wedge, and wherein the rotating drive shaft is rotatable with the collet and wedge within the housing.

2. The wire driver of claim 1, wherein said collet is formed so that the curved ankle surfaces have a concave curvature.

3. The wire driver of claim 1, where said collet is formed so the curved ankle surfaces have a convex curvature.

4. The wire driver of claim 1, wherein: said collet includes a plurality of flexible legs, each of the flexible legs having a distal end; and each of said feet and the curved ankle surfaces extends distally away from the distal end of an associated one of the legs.

5. The wire driver of claim 1, further including a lever that is connected to said wedge to move said wedge between the release position and the grasping position.

6. The wire driver of claim 5, wherein said lever is part of a plural bar linkage assembly.

7. The wire driver of claim 1, wherein said housing adapted for releasable attachment to a handpiece that contains a motor that rotates the drive shaft.

8. A wire driver, said wire driver including:
a rotating drive shaft extending along a longitudinal axis and having a bore extending therein;
a collet extending axially between a proximal end and a distal end, said proximal end is disposed in the bore of the drive shaft and the collet being held fast to the drive shaft for unitary rotational and axial movement therewith and thus coupled to said drive shaft to rotate with said drive shaft, said collet having at said distal end a plurality of feet positioned to surround a wire or pin adapted to be driven into living tissue, said plurality of feet are radially moveable relative to the wire or pin so as to selectively grasp the wire or pin so the wire or pin rotates with the drive shaft, wherein, each foot of said feet has an outwardly located ankle surface having one of a concave profile and a convex profile and the one of the concave profile and the convex profile being radiused such that the curved ankle surface extends distally forward from a proximal portion of the collet, and curves outwardly away from the proximal portion;
a wedge disposed over said collet and at least in part inside the bore of the drive shaft and the wedge being connected to the drive shaft to rotate in unison with the drive shaft and in selective engagement with the curved ankle surfaces and moveable longitudinally relative to the drive shaft and said collet feet so as to have a grasping position in which said wedge surrounds and bears against the feet so as to cause the feet to grasp the wire or pin for rotation with said collet and a release position in which said wedge is spaced from said collet feet so the feet are released from grasping against the wire or pin; wherein said wedge is formed to have an inner surface that defines an open distal end of said wedge, the inner surface being tapered such that extending proximally from a distal end of said collet the inner surface tapers inwardly and a diameter of the tapered surface decreases proximally, and said wedge is disposed over said collet so that when said wedge is in the grasping position, the inwardly tapered inner surface of said wedge abuts the curved ankle surface of said collet feet, further wherein the ankle surface presents an angle of contact against the wedge at a point of contact therebetween with the angle of contact increasing with increased axial displacement of the wedge;
a housing containing said drive shaft, said collet and said wedge, and wherein the rotating drive shaft is rotatable with the collet and wedge within the housing, and
a handpiece for releasable attachment to said housing.

9. The wire driver of claim 8, wherein said collet is formed so that the curved ankle surfaces have a concave curvature.

10. The wire driver of claim 8, where said collet is formed so the curved ankle surfaces have a convex curvature.

11. The wire driver of claim 8, wherein: said collet includes a plurality of flexible legs, each of the flexible leg having a distal end; and each of said feet and the curved ankle surfaces extends distally away from the distal end of an associated one of the legs.

12. The wire driver of claim 8, further including a lever that is connected to said wedge to move said wedge between the release position and the grasping position.

13. The wire driver of claim 12, wherein said lever is part of a plural bar linkage assembly.

\* \* \* \* \*